US011672781B2

(12) United States Patent
Nambiar et al.

(10) Patent No.: US 11,672,781 B2
(45) Date of Patent: Jun. 13, 2023

(54) METAXALONE FORMULATIONS

(71) Applicant: PRANA BIOSCIENCES INC, Southborough, MA (US)

(72) Inventors: Prabu Nambiar, Southborough, MA (US); Binesh Prabhakar, Southborough, MA (US); Geevarghese Easo, Southborough, MA (US)

(73) Assignee: PRANA BIOSCIENCES INC, Southborough, MA (US)

( * ) Notice: Subject to any disclaimer, the term of this patent is extended or adjusted under 35 U.S.C. 154(b) by 302 days.

(21) Appl. No.: 17/047,957

(22) PCT Filed: May 6, 2019

(86) PCT No.: PCT/US2019/030864
§ 371 (c)(1),
(2) Date: Oct. 15, 2020

(87) PCT Pub. No.: WO2019/217286
PCT Pub. Date: Nov. 14, 2019

(65) Prior Publication Data
US 2021/0212995 A1 Jul. 15, 2021

Related U.S. Application Data

(60) Provisional application No. 62/667,680, filed on May 7, 2018.

(51) Int. Cl.
*A61K 31/421* (2006.01)
*A61K 9/10* (2006.01)
*A61K 9/20* (2006.01)

(52) U.S. Cl.
CPC .............. *A61K 31/421* (2013.01); *A61K 9/10* (2013.01); *A61K 9/2013* (2013.01); *A61K 9/2027* (2013.01); *A61K 9/2054* (2013.01)

(58) Field of Classification Search
CPC ...... A61K 31/421; A61K 9/10; A61K 9/2013; A61K 9/2027; A61K 9/2054
See application file for complete search history.

(56) References Cited

U.S. PATENT DOCUMENTS

| 4,291,016 | A | 9/1981 | Nougaret | |
|---|---|---|---|---|
| 7,871,643 | B2 | 1/2011 | Lizio et al. | |
| 2004/0062801 | A1 | 4/2004 | Faour et al. | |
| 2005/0063913 | A1* | 3/2005 | Pruitt .................. | A61K 31/421 424/452 |
| 2005/0163839 | A1 | 7/2005 | Dudhara et al. | |
| 2006/0167069 | A1* | 7/2006 | Dharmadhikari ...... | A61K 45/06 514/376 |
| 2007/0009603 | A1 | 1/2007 | Holm et al. | |
| 2009/0163561 | A1* | 6/2009 | Lorimer .................. | A61P 29/00 548/232 |
| 2012/0093928 | A1 | 4/2012 | Shear et al. | |
| 2012/0263760 | A1* | 10/2012 | Dodd ....................... | A61K 9/14 514/376 |
| 2014/0302127 | A1 | 10/2014 | Dodd et al. | |
| 2015/0352080 | A1* | 12/2015 | Spireas .................. | A61K 47/36 514/376 |

FOREIGN PATENT DOCUMENTS

| CN | 102764243 | A | 11/2012 | |
|---|---|---|---|---|
| EP | 3187176 | A1 | 7/2017 | |
| IN | 2006DE00685 | A | 9/2007 | |
| WO | 99/30690 | A1 | 6/1999 | |
| WO | 2005/016310 | A1 | 2/2005 | |
| WO | 2005/102290 | A1 | 11/2005 | |
| WO | 2007/017513 | A2 | 2/2007 | |
| WO | 2007/075963 | A2 | 7/2007 | |
| WO | 2007/110878 | A1 | 10/2007 | |
| WO | 2008/012115 | A1 | 1/2008 | |
| WO | 2008/044236 | A2 | 4/2008 | |
| WO | 2008/064259 | A2 | 5/2008 | |
| WO | 2009/019662 | A2 | 2/2009 | |
| WO | WO-2009019662 | A2 * | 2/2009 | ........... A61K 31/421 |
| WO | 2009/085637 | A1 | 7/2009 | |
| WO | 2010/118232 | A1 | 10/2010 | |
| WO | 2017/103945 | A1 | 6/2017 | |

OTHER PUBLICATIONS

Nadia Bou-Chacra, Evolution of Choice of Solubility and Dissolution Media After Two Decades of Biopharmaceutical Classification System, Jul. 2017, AAPS Journal, vol. 19 No 4, 989-1001. (Year: 2017).*
Adeline Siew, Dissolution Testing, Nov. 2, 2016, Pharm Tech, vol. 40 Issue 11 (Year: 2016).*
International Search Report and Written Opinion of the International Searching Authority for International Application No. PCT/US2019/030864 dated Aug. 5, 2019.
Gubbala, L.P., et al., "Optimization of Composition and Process for Preparing Metaxalone Nanosuspension using Factorial Design", International Journal of Drug Delivery Technology, vol. 6, No. 3, pp. 79-91 (2016).

* cited by examiner

*Primary Examiner* — Mark L Shibuya
*Assistant Examiner* — Luisalberto Gonzalez
(74) *Attorney, Agent, or Firm* — Heslin Rothenberg Farley & Mesiti P.C.

(57) ABSTRACT

The invention provides a pharmaceutical composition comprising sodium lauryl sulfate, hydroxypropyl methylcellulose (HPMC), a copolymer of vinylpyrrolidone and vinyl acetate, and a therapeutically effective amount of metaxalone or a pharmaceutically acceptable salt thereof. Related processes and methods are also disclosed.

15 Claims, 13 Drawing Sheets

METAXALONE FORMULATIONS

CROSS REFERENCE TO RELATED APPLICATIONS

This application is a U.S. national phase entry under Section 371 of International Application No. PCT/US2019/030864, filed on May 6, 2019, which published as WO2019/217286 on Nov. 14, 2019, which claims priority to U.S. Provisional Application No. 62/667,680, filed on May 7, 2018. The entire contents of each of the prior applications are hereby incorporated herein by reference.

FIELD OF THE INVENTION

The invention relates to new metaxalone formulations, to pharmaceutical compositions comprising said formulations, to processes for the preparation of said formulations and compositions, and to the use of said formulations and compositions in the treatment of conditions, e.g., musculoskeletal conditions and musculoskeletal pain.

BACKGROUND OF THE INVENTION

Metaxalone is a centrally acting skeletal muscle relaxant. Indicated for the treatment and relief of discomforts associated with acute, painful musculoskeletal conditions, metaxalone is frequently prescribed to relax muscles and relieve pain caused by strains, sprains, and other musculoskeletal conditions. Skelaxin® (metaxalone) 800 mg tablets are currently marketed by Pfizer (Skelaxin is a registered trademark of King Pharmaceuticals Research and Development, LLC). A Skelaxin 400-mg dosage strength was previously approved for marketing, but is listed in the "Discontinued Drug Product List" section of the Orange Book, although a generic 400-mg dosage form is available.

Metaxalone drug substance is a crystalline material that is practically insoluble in aqueous media. Aqueous solubility of metaxalone is less than 50 ug/ml and independent of pH across the physiological pH range found in the GI tract. This type of solubility profile can lead to a slow rate of absorption and incomplete bioavailability which in turn may require higher doses. Metaxalone is also associated with a significant food effect.

The recommended dose of metaxalone is 800 mg three or four times daily. Possible side effects of metaxalone can be related to CNS depression, and can include nausea, vomiting, drowsiness, dizziness, headache, and irritability, as well as hepatotoxicity and hemolytic anemia.

Thus, a need exists for metaxalone formulations having improved properties such as improved solubility, improved bioavailability, elimination or reduction of food effect, and/or faster onset of action, in order to further improve upon patient outcomes.

In this specification, where a document, act or item of knowledge is referred to or discussed, this reference or discussion is not an admission that the document, act or item of knowledge or any combination thereof was, at the priority date, publicly available, known to the public, part of common general knowledge, or otherwise constitutes prior art under the applicable statutory provisions; or is known to be relevant to an attempt to solve any problem with which this specification is concerned.

SUMMARY OF THE INVENTION

Briefly, the present invention satisfies the need for improved metaxalone formulations.

The present invention may address one or more of the problems and deficiencies of the art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In a first aspect, the invention provides a metaxalone formulation comprising metaxalone or a pharmaceutically acceptable salt thereof, sodium lauryl sulfate, hydroxypropyl methylcellulose (HPMC), and a copolymer of vinylpyrrolidone and vinyl acetate. Some embodiments of the formulation have advantages such as improved solubility, improved bioavailability, elimination or reduction of food effect, and/or faster onset of action.

In another aspect, the invention provides a process for preparing (also known as a method for manufacturing) embodiments of a formulation or pharmaceutical composition as described above.

Another aspect of the invention involves use of the inventive formulations (e.g., pharmaceutical compositions) for purposes of treating conditions and/or symptoms of conditions (e.g., musculoskeletal conditions and/or symptoms associated therewith).

Certain embodiments of the presently-disclosed metaxalone formulations, pharmaceutical compositions, and related processes and methods have several features, no single one of which is solely responsible for their desirable attributes. Without limiting the scope of the inventive formulations, compositions, processes, and methods as defined by the claims that follow, their more prominent features will now be discussed briefly. After considering this discussion, and particularly after reading the section of this specification entitled "Detailed Description of the Invention," one will understand how the features of the various embodiments disclosed herein provide a number of advantages over the current state of the art. For example, the invention provides embodiments of metaxalone formulations that have improved solubility, bioavailability, $C_{max}$ and/or $t_{max}$, and/or minimized or elimination of food effect as compared to other metaxalone formulations, including the presently-marketed metaxalone formulation. These and other features and advantages of this invention will become apparent from the following detailed description of the various aspects of the invention taken in conjunction with the appended claims and the accompanying drawings.

BRIEF DESCRIPTION OF THE DRAWINGS

The present invention will hereinafter be described in conjunction with the following drawing figures, wherein:

FIG. 5C, 40° C./75% RH).

DETAILED DESCRIPTION OF THE INVENTION

Figure 1:
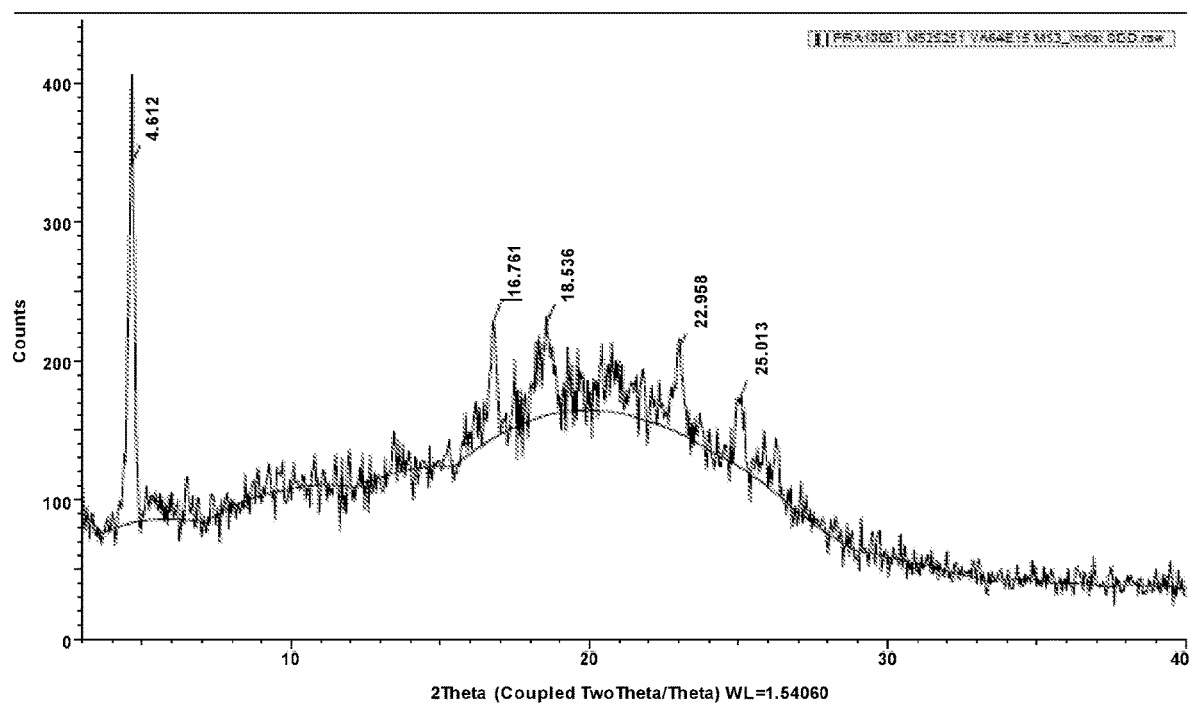
FIG. 1 shows an XRPD diffractogram of an embodiment of an inventive formulation.

Reference will now be made in detail to certain embodiments of the invention. While the invention will be described in conjunction with the enumerated embodiments, it will be understood that they are not intended to limit the invention to those embodiments. Rather, the invention is intended to cover all alternatives, modifications and equivalents that may be included within the scope of the present invention as defined by the claims. The present invention is not limited to the methods and materials described herein but include any methods and materials similar or equivalent to those described herein that could be used in the practice of the present invention. In the event that one or more of the incorporated literature references, patents or similar materials differ from or contradict this application, including but not limited to defined terms, term usage, described techniques or the like, this application controls.

The terms "drug", "agent", "active pharmaceutical ingredient (API)", "drug substance", "active", or "active ingredient (AI)" may be used indistinguishably throughout this disclosure to refer to the substance in a "pharmaceutical product" (i.e., a "medicine" or "medication" or "drug product") that is biologically active. Metaxalone is an API in the inventive compositions. Some medications may contain more than one active ingredient.

As used herein, a "pharmaceutical composition" comprises the API and one or more pharmaceutically acceptable excipients. The term "pharmaceutically acceptable," as used herein, refers to a component that is, within the scope of sound medical judgment, suitable for use in contact with the tissues of humans and other mammals without undue toxicity, irritation, allergic response and the like, and is commensurate with a reasonable benefit/risk ratio. Preferably, a composition of this invention is formulated for pharmaceutical use ("a pharmaceutical composition"), wherein the carrier is a pharmaceutically acceptable carrier. The carrier(s) must be "acceptable" in the sense of being compatible with the other ingredients of the formulation and, in the case of a pharmaceutically acceptable carrier, not deleterious to the recipient thereof in amounts typically used in medicaments.

The term "dosage form" or "unit dosage form", as used herein, refers to a structure, such as a capsule, a pill, a tablet, an emulsion or a syrup, prepared according to a specific procedure from a formulation or pharmaceutical composition that delivers a "dose", or measured quantity of the API to the patient. Dosage forms provide an easily controllable dosage of the drug and enable patient compliance with the prescribed regimen. Various dosage forms may exist for the same compound, since different medical conditions may warrant different routes of administration.

In some embodiments, the dosage form disclosed herein is an oral solid dosage form. In some embodiments, said oral solid dosage form is a capsule, cachet, or tablet. In some embodiments, the dosage form may be administered several times in a period of 24 hours in order to achieve a desired pharmacological effect.

The term "gastric fluid" refers to the endogenous fluid medium of the stomach, including water and secretions. "Simulated gastric fluid" means any fluid that is generally recognized as providing a useful substitute for authentic gastric fluid in in-vitro experiments designed to assess the chemical or biological behavior of substances in the stomach. One such simulated gastric fluid is aqueous 0.1 N HCl. It will be understood that the term "gastric fluid" used throughout the disclosure encompasses both the authentic (i.e. endogenous) gastric fluid and simulated gastric fluids.

As used herein, a "therapeutically effective amount" of a drug or agent is an amount of a drug or agent (e.g., metaxalone) that, when administered to a subject with a condition will have the intended therapeutic effect, e.g., alleviation, amelioration, palliation or elimination of one or more manifestations of the condition in the subject. The full therapeutic effect does not necessarily occur by administration of one dose and may occur only after administration of a series of doses. Thus, a therapeutically effective amount may be administered in one or more administrations. The term "therapeutically effective amount" as used herein also means that amount of active compound or pharmaceutical agent that elicits the biological or medicinal response in a tissue, system, animal or human that is being sought by a researcher, veterinarian, medical doctor or other clinician. The therapeutically or pharmaceutically effective amount of the compound to be administered will be governed by such considerations, and is the minimum amount necessary to ameliorate, cure or treat the condition or disorder or one or more of its symptoms.

Figure 4A:
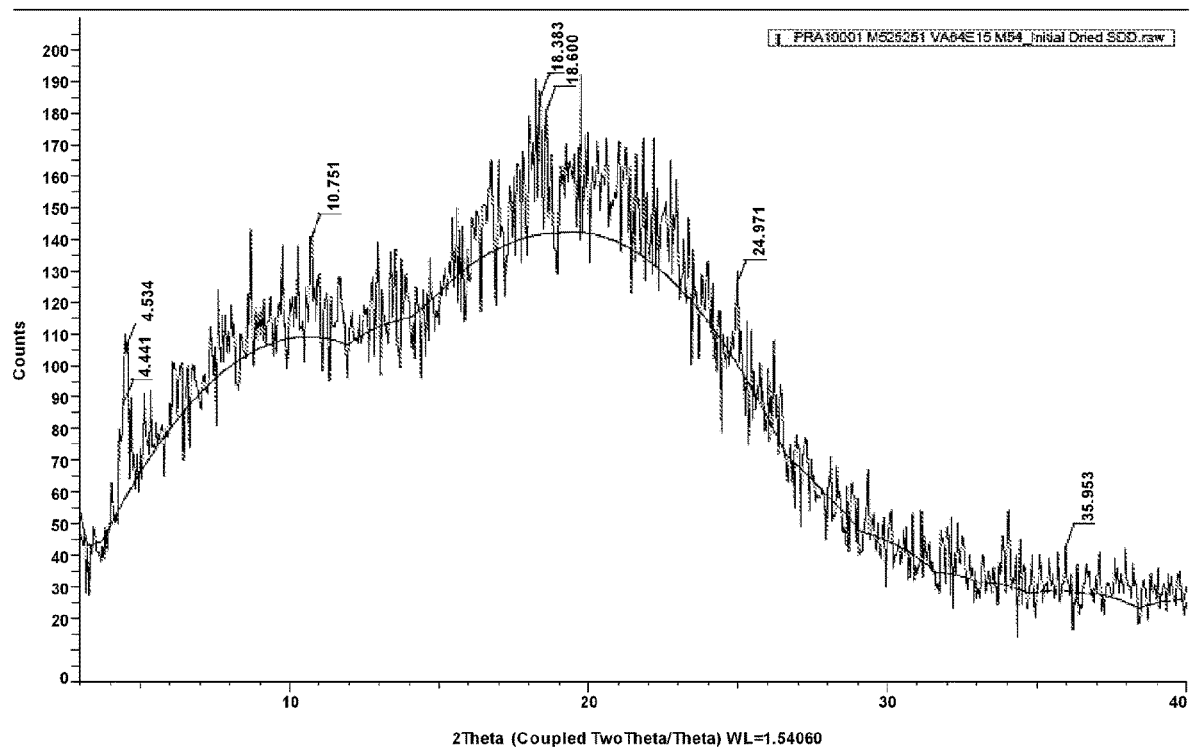
FIGS. 4A and 4B are XRPD diffractograms of an embodiment of an inventive formulation prior to, and after storage at 40° C./75% RH for six weeks.
Figure 4B:
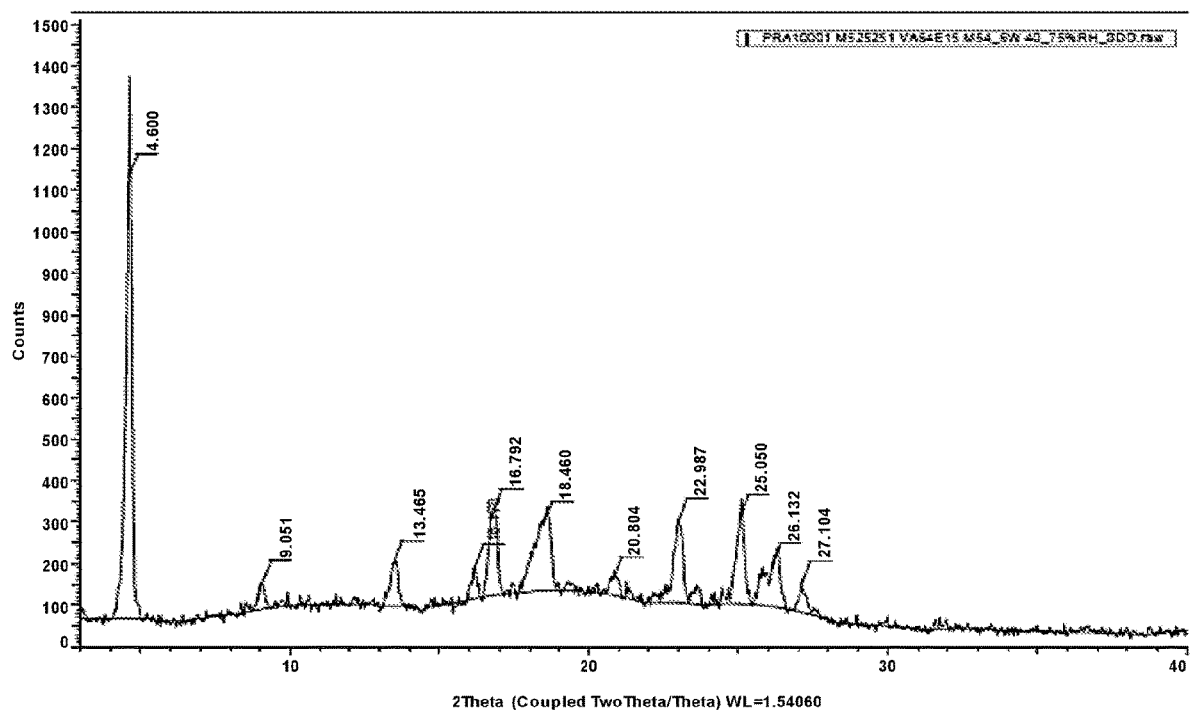

Metaxalone is indicated for the treatment and relief of discomforts associated with acute, painful musculoskeletal conditions. Metaxalone drug substance is a crystalline material, the XRPD diffractogram of which is shown in FIG. 4B. The drug substance is practically insoluble in aqueous media independent of pH across the physiological pH range found in the GI tract and exhibits a slow and inconsistent rate of dissolution. This type of profile can lead to a slow rate of absorption and/or incomplete bioavailability which in turn may require higher doses. Currently-marketed metaxalone tablets are also associated with a significant food effect. Individual subject exposure in the presence of varying food compositions may impact both the rate and extent of drug absorption which in turn has the potential to impact its clinical profile. Embodiments of the invention improve both the biopharmaceutical profile of metaxalone and its pharmacokinetics to maximize drug delivery and further improve upon patient outcomes.

In a first aspect, the invention provides a metaxalone formulation comprising metaxalone or a pharmaceutically acceptable salt thereof, sodium lauryl sulfate, hydroxypropyl methylcellulose (HPMC), and a copolymer of vinylpyrrolidone and vinyl acetate.

In some embodiments, the formulation is a pharmaceutical composition that comprises sodium lauryl sulfate, hydroxypropyl methylcellulose (HPMC), a copolymer of vinylpyrrolidone and vinyl acetate, and a therapeutically effective amount of metaxalone or a pharmaceutically acceptable salt thereof.

Metaxalone (5-[(3,5-dimethylphenoxy)methyl]-2-oxazolidinone) is an oxazolidinone with centrally-acting skeletal muscle relaxant properties, having the structure:

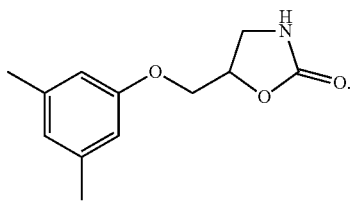 [SMILES: Cc1cc(C)cc(OCC2CNC(=O)O2)c1]

Metaxalone is a muscle relaxant currently used for treating painful musculoskeletal conditions. Metaxalone is indicated as an adjunct to rest, physical therapy, and other measures for the relief of discomforts associated with acute, painful musculoskeletal conditions.

The copolymer of vinylpyrrolidone and vinyl acetate in the inventive embodiments is a copolymer of 1-vinyl-2-pyrrolidone (VP) and vinyl acetate (VAc). In some embodiments, the ratio of VP:VAc in the copolymer is about 5:4 to 7:4 by mass, e.g., about 6:4 by mass. In some embodiments, the copolymer is of formula (I):

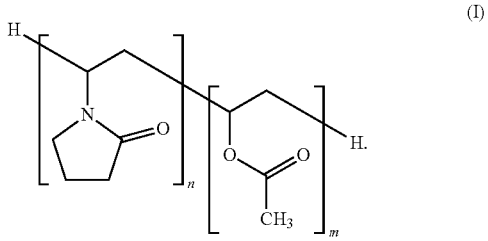

In some embodiments of copolymers of formula (I), 0.8 m≤n≤1.6 m (e.g., 0.8 m, 0.9 m, 1.0 m, 1.1 m, 1.2 m, 1.3 m, 1.4 m, 1.5 m, 1.6 m, 1.7 m, or 1.8 m, including any and all ranges and subranges therein), for example, m≤n≤1.4 m, or 1.1 m≤n≤1.3 m, or n 1.2 m, wherein m and n are the number of repeating units from polyvinyl acetate and polyvinyl pyrrolidone, respectively.

In some embodiments, the copolymer of vinylpyrrolidone and vinyl acetate is the polymerization product of a monomer mixture that consists of vinylpyrrolidone and vinyl acetate (i.e., the monomer mixture does not comprise other polymerizable monomers). In such embodiments, the monomer residues present in the copolymer consist of residues of the vinylpyrrolidone and vinyl acetate.

In some embodiments, the copolymer of vinylpyrrolidone and vinyl acetate is Kollidon VA 64 (available from BASF as Product No. 95405-2-43), which is a vinylpyrrolidone-vinyl acetate copolymer that is soluble in both water and alcohol.

In some embodiments, the formulation (e.g., pharmaceutical composition) comprises:

40 to 60 weight percent (wt %) metaxalone or a pharmaceutically acceptable salt thereof (e.g., 40, 41, 42, 43, 44, 45, 46, 47, 48, 49, 50, 51, 52, 53, 54, 55, 56, 57, 58, 59, or 60 wt %), including any and all ranges and subranges therein (e.g., 45 to 55 wt %, 48 to 52 wt %, etc.);

0.2 to 5 wt % sodium lauryl sulfate (e.g., 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 wt %), including any and all ranges and subranges therein (e.g., 0.5 to 2 wt %, 0.8 to 1.2 wt %, etc.);

15 to 35 wt % HPMC (e.g., 15, 16, 17, 18, 19, 20, 21, 22, 23, 24, 25, 26, 27, 28, 29, 30, 31, 32, 33, 34, or 35 wt %), including any and all ranges and subranges therein (e.g., 20 to 30 wt %, 23 to 27 wt %, etc.); and 15 to 35 wt % copolymer of vinylpyrrolidone and vinyl acetate (e.g., 15, 16, 17, 18, 19, 20, 21, 22, 23, 24, 25, 26, 27, 28, 29, 30, 31, 32, 33, 34, or 35 wt %), including any and all ranges and subranges therein (e.g., 20 to 30 wt %, 23 to 27 wt %, etc.).

In some embodiments, the inventive pharmaceutical composition comprises 50 to 100 wt % (e.g., 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 wt %, or any range or subrange therein) of an embodiment of a formulation as described in the preceding paragraph, with any remaining balance comprising one or more further agents (e.g., one or more disintegrants, diluents, glidants, lubricants, acidulants, stabilizers, suspending agents, fillers, binders, plasticizers, or release aids, or other pharmaceutically acceptable carriers, excipients, or adjuvants, or non-metaxalone active ingredients).

In some embodiments, the pharmaceutical composition is a solid dosage form for oral administration. In particular embodiments, the solid dosage form is a tablet or capsule. In more particular embodiments, the solid dosage form is a tablet.

In some embodiments, the pharmaceutical composition comprises 100 to 1600 mg metaxalone or a pharmaceutically acceptable salt thereof (e.g., 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, 1510, 1520, 1530, 1540, 1550, 1560, 1570, 1580, 1590, or 1600 mg metaxalone or a pharmaceutically acceptable salt thereof, including any and all ranges and subranges therein). In particular embodiments, the pharmaceutical composition comprises 200 mg or 300 mg or 400 mg or 450 mg or 800 mg metaxalone or a pharmaceutically acceptable salt thereof.

In some embodiments, the pharmaceutical composition is a tablet or capsule comprising a spray-dried amorphous dispersion. In some embodiments, the metaxalone or pharmaceutically acceptable salt thereof, sodium lauryl sulfate, hydroxypropyl methylcellulose (HPMC), and copolymer of vinylpyrrolidone and vinyl acetate are comprised within the spray-dried amorphous dispersion. Persons having ordinary skill in the art will readily appreciate that the particle size of the spray-dried amorphous dispersion can be varied by altering spray-drying parameters. All desirable particle sizes are intended to be encompassed by embodiments of the inventive pharmaceutical compositions. Still, in some non-limiting embodiments, the spray-dried amorphous dispersion has an average particle size of 0.5 to 100 µm (e.g., 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 µm), including any and all ranges and subranges therein (e.g., 0.5 to 25 µm, 1 to 18 µm, 1.5 to 16 µm, etc.).

In some embodiments, the pharmaceutical composition additionally comprises one or more further agents. For example, in some embodiments, the pharmaceutical composition additionally comprises one or more agents selected from suitable disintegrants, diluents, glidants, lubricants, acidulants, stabilizers, suspending agents, fillers, binders, plasticizers, release aids, and other pharmaceutically acceptable carriers excipients, and adjuvants. Persons having ordinary skill in the art are well familiar with selecting various further agents to include in a formulation or pharmaceutical composition; it is contemplated that any desirable agents may be included in inventive embodiments.

In some embodiments, the pharmaceutical composition is in an oral dosage form comprised of a core and a coating. In some embodiments, the coating represents from 2 to 10 wt % of the total weight of the formulation. In other embodiments, the pharmaceutical composition is in an oral dosage form that does not comprise a coating.

In some embodiments, the inventive formulations (e.g., pharmaceutical compositions) provide significantly improved solubility and/or bioavailability as compared to currently-marketed compositions (e.g., the Reference Listed Drug (RLD), Skelaxin). For example, some embodiments exhibit improved bioavailability with respect to pharmacokinetic (PK) parameters, $C_{max}$, $t_{max}$, and AUC0-t compared to RLD. Thus, embodiments of the invention allow for equally or improved efficaciousness in treating a patient suffering from a condition (e.g., a painful musculoskeletal condition) while administering to the patient a lower amount of the API.

In some embodiments, the inventive formulation has a dissolution rate such that, when the composition is tested using USP Apparatus 2 (paddle) set to rotation speed of 100 RPM in 900 mL of 0.5% sodium lauryl sulfate (SLS), pH 2.0, at 37° C., at least 35% (e.g., at least 35, 36, 37, 38, 39, 40, 41, 42, 43, 44, or 45%) of the metaxalone dissolves in 10 minutes or less.

In some embodiments, the inventive formulation comprises a spray dried dispersion (SDD) powder having a moisture level of 4 wt % or less. In some embodiments, the inventive formulation comprises a SDD powder having a moisture level of 1 to 4 wt % (e.g., 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0 wt %), including any and all ranges and subranges therein (e.g., 1.5 to 4 wt %, 2 to 4 wt %, 1.5 to 3.5 wt %, etc.).

"Pharmacokinetic parameters" (also referred to herein as "PK parameters") describe the in-vivo characteristics of an active agent (herein, metaxalone) over time, such as plasma concentration (C), $C_{max}$, $C_n$, $t_{max}$, and AUC. As is well known by persons having ordinary skill in the art, "$C_{max}$" is the measured concentration of the active agent in plasma at the point of maximum concentration. "$C_n$" is the measured concentration of an active agent in the plasma at about n hours after administration. The term "$t_{max}$" refers to the time at which the measured concentration of an active agent in the plasma is the highest after administration of the active agent. "AUC" is the area under the curve of a graph of the measured concentration of an active agent (typically plasma concentration) vs. time, measured from one time point to another time point. For example, $AUC_{0-t}$ is the area under the curve of plasma concentration versus time from time 0 to time t. The $AUC_{0-\infty}$ is the calculated area under the curve of plasma concentration versus time from time 0 to time infinity.

In some embodiments, the inventive formulation/pharmaceutical composition provides, in vivo, for a dosage containing 400 mg metaxalone or a pharmaceutically acceptable salt thereof, a $C_{max}$ of 1400 to 6000 ng/mL (e.g., 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, or 6000 ng/mL), including any and all ranges and subranges therein (e.g., 1500 to 6000 ng/mL, 2000 to 6000 ng/mL, 2200 to 6000 ng/mL, etc.). In some embodiments, the inventive formulation/pharmaceutical composition provides, in vivo, a $C_{max}$ that is proportional to a $C_{max}$ of 1400 to 6000 for a dosage containing 400 mg metaxalone or a pharmaceutically acceptable salt thereof (thus, for example, in some embodiments, the inventive formulation/pharmaceutical composition provides, in vivo, for a dosage containing 800 mg metaxalone or a pharmaceutically acceptable salt thereof, a $C_{max}$ of 2800 to 12000 ng/mL, including any and all ranges and subranges therein).

In some embodiments, the inventive formulation/pharmaceutical composition provides, in vivo, a $t_{max}$ of 0.5 to 3 hours (e.g., 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 hours), including any and all ranges and subranges therein (e.g., 0.5 to 1.9 hours, 0.5 to 1.8 hours, 0.5 to 1.5 hours, 1 to 1.9 hours, 1 to 1.8 hours, etc.)

In another aspect, the invention provides a process for preparing (also known as a method for manufacturing) embodiments of a formulation or pharmaceutical composition as described above.

Embodiments of the inventive metaxalone formulations and compositions can be formulated in accordance with methods that are standard in the art (see e.g., Remington: the Science and Practice of Pharmacy 21st Ed. 2005, University Sciences in Philadelphia Pa. or Developing Solid Oral Dosage Forms—Pharmaceutical Theory and Practice, 1st Ed; Academic Press; Burlington, Mass.).

In some embodiments, metaxalone formulations are prepared by spray-drying metaxalone API and other formulation constituents to form an amorphous spray dried dispersion, which is a compressible powder. Spray drying apparatuses (e.g., Buchi, Yamato, etc.) are well known in the art.

Various nozzle orifice sizes may be used during spray-drying. In some embodiments, samples are spray-dried using a nozzle orifice size of 100 µm to 5000 µm (e.g., 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, or 5000 µm), including any and all ranges and subranges therein.

In some embodiments, the process comprises forming a capsule or tablet comprising the formulation or pharmaceutical composition.

In some embodiments, the process comprises spray-drying to form an amorphous dispersion comprising the formulation or pharmaceutical composition.

In some embodiments, the process comprises mixing metaxalone or a pharmaceutically acceptable salt thereof and other formulation constituents in a solvent prior to spray drying. In some embodiments, the solvent is a single solvent, whereas in other embodiments, the solvent is a solvent mixture. In some embodiments, the solvent comprises methyl ethyl ketone, acetone, methanol, and/or water. In some embodiments, the solvent comprises a mixture of a suitable organic solvent and water. In some embodiments, the solvent comprises: 75 to 95 vol % (e.g., 75, 76, 77, 78, 79, 80, 81, 82, 83, 84, 85, 86, 87, 88, 89, 90, 91, 92, 93, 94, or 95 vol %), including any and all ranges and subranges therein (e.g., 80 to 92 vol %, 85 to 91 vol %, etc.) organic solvent (e.g., methanol); and 5 to 25 vol % (e.g., 5, 6, 7, 8, 9, 10, 11, 12, 13, 14, 15, 16, 17, 18, 19, 20, 21, 22, 23, 24, or 25 vol. %), including any and all ranges and subranges therein (e.g., 8 to 20 vol %, 9 to 15 vol %, etc.) water.

Another aspect of the invention involves use of the inventive formulations (e.g., pharmaceutical compositions) for purposes of treating conditions and/or symptoms of conditions (e.g., musculoskeletal conditions and/or symptoms associated therewith).

In some embodiments, the invention provides a method of treating a subject comprising administering to the subject a formulation or pharmaceutical composition as described herein. In some embodiments, the invention provides a method for treating a musculoskeletal condition or musculoskeletal pain. For example, in some embodiments, the invention provides, inter alia:

A method for the treatment of pain, which method comprises administering to a subject in need thereof a formulation or pharmaceutical composition as described herein.

A method for the treatment of a musculoskeletal condition, which method comprises administering to a subject in need thereof a formulation or pharmaceutical composition as described herein.

A method for providing pain relief (e.g., musculoskeletal pain relief), which method comprises administering to a subject in need thereof a formulation or pharmaceutical composition as described herein.

A method for providing pain relief (e.g., pain relief for acute, painful musculoskeletal conditions), which method comprises administering to a subject in need thereof a formulation or pharmaceutical composition as described herein.

A method for treating muscle spasms, which method comprises administering to a subject in need thereof a formulation or pharmaceutical composition as described herein.

A method for treating back pain, which method comprises administering to a subject in need thereof a formulation or pharmaceutical composition as described herein.

A method for relaxing muscles, which method comprises administering to a subject a formulation or pharmaceutical composition as described herein.

A method for relieving pain caused by strains, sprains, or other musculoskeletal conditions, which method comprises administering to a subject a formulation or pharmaceutical composition as described herein.

A formulation or pharmaceutical composition as described herein for use as described herein.

Use of a formulation or pharmaceutical composition as described herein for the treatment of a condition or symptom as described herein.

The use of a formulation or pharmaceutical composition as described herein for the manufacture of a medicament for treatment of a condition or symptom as described herein.

In some embodiments, the invention provides uses and methods as described herein, comprising use of (e.g. administering) 200 mg to 3200 mg of metaxalone or a pharmaceutically acceptable salt thereof a day (e.g., 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3100, or 3200 mg metaxalone or a pharmaceutically acceptable salt thereof), including any and all ranges and subranges therein. In some embodiments, the daily dose is 400 mg to 2000 mg, e.g., 450 to 1600 mg.

In some embodiments, the formulation (e.g., pharmaceutical composition) described herein is administered up to 4 times in a 24-hour period (e.g., 1, 2, 3, or 4 times in a 24-hour period). In some embodiments, the formulation is a dosage form comprising metaxalone or a pharmaceutically acceptable salt thereof (e.g., 200 mg, 250 mg, 400 mg, 450 mg, etc.), and is administered 1, 2, 3, or 4 times daily, as needed.

In some embodiments, the invention provides uses and methods as described herein, comprising administering the metaxalone formulation (e.g., pharmaceutical composition) to a subject who is in the fed state.

In some embodiments, the formulation (e.g., pharmaceutical composition) described herein is administered with one or more meals. In some embodiments, the formulation (e.g., pharmaceutical composition) described herein is administered with a meal.

The terms "disorder" and "condition" may be used interchangeably herein to refer to a medical or pathological condition or symptom (e.g., a musculoskeletal condition, or musculoskeletal pain).

As used herein, the terms "subject" and "patient" are used interchangeably. The terms "subject" and "patient" refer to an animal (e.g., a bird such as a chicken, quail or turkey, or a mammal), e.g., a "mammal" including a non-primate (e.g., a cow, pig, horse, sheep, rabbit, guinea pig, rat, cat, dog, mouse) and a primate (e.g., a monkey, chimpanzee, human), and, in particular, a human. In some embodiments, the subject is a non-human animal such as a farm animal (e.g., a horse, cow, pig or sheep), or a pet (e.g., a dog, cat, guinea pig or rabbit). In some embodiments, the subject is a human.

Embodiments of the invention relate to treating subjects having, or predisposed to having a particular condition or symptom. A "subject in need thereof" is an individual who suffers from, is suffering from, or is likely to or predisposed to suffer from a condition or symptom as discussed herein (e.g., a musculoskeletal condition, or musculoskeletal pain).

"Treat", "treating" or "treatment" with regard to a disorder or condition (including a symptom) refers to alleviating or abrogating the disorder, condition or symptom, or the cause and/or the effects of the disorder, condition, or symptom. Treatment can involve administering a formulation (e.g., pharmaceutical composition) described herein to a subject diagnosed with a disorder or condition, and may involve administering the formulation to a subject who has or does not have active symptoms. Conversely, treatment may involve administering the formulation to a subject at risk of developing a particular disorder or symptom, or to a subject reporting one or more of the physiological symptoms of a disorder or condition, even though a diagnosis of such disorder or condition may not have been made.

As used herein, "treating" or "treatment" of a condition or subject refers to taking steps to obtain beneficial or desired results, including clinical results. For purposes of this disclosure, beneficial or desired clinical results include, but are not limited to, alleviation or amelioration of one or more disorder, symptom, or condition that arises as a result of a musculoskeletal condition or disorder.

The terms "administer", "administering" or "administration" in reference to a dosage form of the invention refer to the act of introducing the dosage form into the system of a subject in need of treatment. When a dosage form of the invention is given in combination with one or more other active agents (in their respective dosage forms), "administration" and its variants are each understood to include concurrent and/or sequential introduction of the dosage form and the other active agents.

Administration of any of the described dosage forms includes parallel administration, co-administration or sequential administration, in which the therapies are administered at approximately the same time, e.g., within about a few seconds to a few hours of one another.

The term "fed mode", as used herein, refers to a state which is typically induced in a patient by the presence of food in the stomach. As described in U.S. Pat. No. 6,683,102, administration of metaxalone with food can increase both the rate and extent of absorption via the oral dosage form in human subjects.

Administration of a dosage form "with a meal", as used herein, refers to administration during, immediately preceding, or after the ingestion of food or drink. When a dosage form is administered after a meal, it may be administered about 1, 2, 3, 4, 5, 10, 15, 30, 45, or 60 minutes, or up to several hours (e.g., 1.5, 2, 2.5, 3, or 3.5 hours) after completion of a meal. In some embodiments, the dosage form may be administered about 1, 2, 3, 4, 5, 10, 15, 30, 45, or 60 minutes, or up to several hours (e.g., 1.5, 2, 2.5, 3, or 3.5 hours) before a meal.

Examples

The invention will now be illustrated, but not limited, by reference to the specific embodiment described in the following examples.

Spray-Dried Metaxalone Formulation Examples

Embodiments of spray drying metaxalone API lead to the formation of homogeneous solid dispersions of the drug in concentration enhancing polymers. Embodiments of the amorphous mixture result in significant improvement to both in-vitro dissolution and in-vivo bioavailability.

Preparation of Example Mixtures

Materials are weighed individually as per the compositions, according to Table I, below. Metaxalone is dissolved in an appropriate solvent and then the Additional Formulation Materials Used (as recited in Table I) are added, and the mixture is stirred well to completely dissolve additional materials used, thereby forming an example mixture.

Spray Drying Process

Example mixtures are spray dried using a Yamato Spray Dryer ADL311S. Spray drying involves evaporation of solvents from an atomized feed by mixing the sprayed example mixtures and a drying medium, typically air or an inert gas such as nitrogen. The drying proceeds until the desired residual solvent content is reached in the sprayed particles and the product is then obtained. Secondary drying, comprising controlling temperature during drying, is performed. This is because residual solvent content has potential effects on crystallization kinetics of the amorphous form. Wet spray dried dispersion (SDD) has a lower glass transition temperature (Tg) than dried SDD, and material held near its glass transition temperature is more likely to crystallize. The resulting spray dried dispersion formulations are compressible powder containing the active drug substance, metaxalone.

Spray drying of samples was performed using a nozzle orifice size of 0.7 mm, inlet temperatures of about 55 to 75° C., outlet temperatures of about 28 to 48° C., air flow rates of about 0.10 to 0.14 Mpa, sample feed rates of about 2 mL/min, and aspirator (blower) of about 1.5 to 3.5 (flow rate of drying air of about 0.02 to 0.20 m$^3$/min), with varying drying times resulting in spray dried dispersion (SDD) powders having moisture levels of under 4 wt %.

Table I summarizes some of the formulation embodiments tested in arriving at the present invention. As recited in the table, VP/VA refers to a copolymer of vinylpyrrolidone and vinyl acetate. For the embodiments tested, the VP/VA is Kollidon VA 64. SLS is sodium lauryl sulfate. HPMC is hydroxypropyl methylcellulose. HPMC-AS is hydroxypropyl methylcellulose functionalized with a mixture of monosuccinic acid and acetic acid esters. For the embodiments tested, the HPMC-AC is Affinisol HPMCAS, marketed by Dow. MEK is methyl ethyl ketone.

TABLE I

| | | Add'l Formulation Materials Used (g) | | | | | |
|---|---|---|---|---|---|---|---|
| Formulation No. | Metaxalone (g) | VP/VA (g) | SLS (g) | HPMC-AS (g) | HPMC (g) | Solvent | Solvent (mL) |
| 1 | 5.0089 | 0 | 0 | 0 | 5.0073 | Acetone | 315 ml |
| | | | | | | Water | 35 ml |
| 2 | 5.0085 | 0 | 0 | 5.0041 | 0 | MEK | 375 ml |
| 3 | 5.0073 | 5.0061 | 0 | 0 | 0 | MEK | 100 ml |
| 4 | 10.0157 | 5.0206 | 0 | 0 | 5.0229 | Acetone | 360 ml |
| | | | | | | Water | 40 ml |
| 5 | 10.0276 | 5.007 | 0 | 0 | 5.0164 | Acetone | 360 ml |
| | | | | | | Water | 40 ml |
| 6 | 5.0341 | 2.5082 | 0 | 0 | 2.5021 | Acetone | 180 ml |
| | | | | | | Water | 20 ml |
| 7 | 5.0389 | 2.5081 | 0 | 0 | 2.5149 | Acetone | 180 ml |
| | | | | | | Water | 20 ml |
| 8 | 10.0809 | 0 | 0 | 10.0799 | 0 | MEK | 750 ml |
| 9 | 10.0073 | 0 | 0 | 10.0069 | 0 | MEK | 750 ml |
| 10 | 9.0072 | 0 | 0 | 9.0052 | 0 | MEK | 675 ml |

TABLE I-continued

| Formulation No. | Metaxalone (g) | VP/VA (g) | SLS (g) | HPMC-AS (g) | HPMC (g) | Solvent | Solvent (mL) |
|---|---|---|---|---|---|---|---|
| 11 | 10.0079 | 10.0072 | 0.2009 | 0 | 0 | MEK/Methanol<br>Water | 280 ml/50 ml<br>40 ml |
| 12 | 10.0154 | 10.0256 | 0.2029 | 0 | 0 | MEK/Methanol<br>Water | 280 ml/50 ml<br>40 ml |
| 13 | 5.0092 | 5.0077 | 0.101 | 0 | 0 | MEK/Methanol<br>Water | 145 ml/20 ml<br>20 ml |
| 14 | 7.0226 | 7.0269 | 0.1413 | 0 | 0 | MEK/Methanol<br>Water | 125 ml/35 ml<br>15 ml |
| 15 | 7.0201 | 7.0072 | 0.1443 | 0 | 0 | MEK/Methanol<br>Acetone/Water | 205 ml/20 ml<br>20 ml/15 ml |
| 16 | 9.9038 | 0 | 0.2007 | 9.907 | 0 | MEK<br>Water | 610 ml<br>65 ml |
| 17 | 5.0024 | 0 | 0.1003 | 4.9012 | 0 | MEK<br>Water | 337 ml<br>37 ml |
| 18 | 14.0113 | 6.0042 | 0.2014 | 0 | 0 | MEK/Methanol<br>Water | 280 ml/80 ml<br>40 ml |
| 19 | 14.0279 | 6.0293 | 0.2014 | 0 | 0 | MEK/Methanol<br>Water | 280 ml/80 ml<br>40 ml |
| 20 | 7.0054 | 3.0021 | 0.1014 | 0 | 0 | MEK/Methanol<br>Water | 140 ml/40 ml<br>20 ml |
| 21 | 16.0008 | 0 | 0.1002 | 3.9033 | 0 | MEK<br>Water | 300 ml<br>35 ml |
| 22 | 16.0032 | 0 | 0.1013 | 3.9042 | 0 | MEK<br>Water | 300 ml<br>35 ml |
| 23 | 8.0011 | 0 | 0.0506 | 1.9504 | 0 | MEK<br>Water | 150 ml<br>17 ml |
| 24 | 8.0023 | 0 | 0.1004 | 1.9006 | 0 | MEK<br>Water | 150 ml<br>17 ml |
| 25 | 16.003 | 0 | 0.1016 | 3.9048 | 0 | MEK<br>Water | 300 ml<br>35 ml |
| 26 | 9.0104 | 0 | 0.0518 | 0.9525 | 0 | MEK<br>Water | 150 ml<br>17 ml |
| 27 | 8.0053 | 0 | 0.0502 | 1.9533 | 0 | MEK<br>Water | 150 ml<br>17 ml |
| 28 | 4.8074 | 0 | 0.0301 | 1.1772 | 0 | MEK<br>Water | 90 ml<br>10 ml |
| 29 | 25.0221 | 12.5241 | 0.5068 | 0 | 12.5048 | Methanol<br>Water | 900 ml<br>100 ml |
| 30 | 25.0489 | 12.5247 | 0.5059 | 0 | 12.5231 | Methanol<br>Water | 900 ml<br>100 ml |
| 31 | 10.0278 | 5.0197 | 0.2039 | 0 | 5.0139 | Methanol<br>Water | 360 ml<br>40 ml |
| 32 | 5.0138 | 2.5047 | 0.1019 | 0 | 2.5045 | Methanol<br>Water | 180 ml<br>20 ml |
| 33 | 15.0093 | 7.5076 | 0.3038 | 0 | 7.5129 | Methanol<br>Water | 540 ml<br>60 ml |
| 34 | 10.0291 | 5.0118 | 0.2036 | 0 | 5.0202 | Acetone | 360 ml |
| 35 | 5.0124 | 2.5196 | 0.1047 | 0 | 2.5221 | Acetone | 180 ml |
| 36 | 16.0216 | 0 | 0 | 4.0217 | 0 | MEK | 335 ml |
| 37 | 25.0091 | 12.5089 | 0.5048 | 0 | 12.5059 | Methanol<br>Water | 900 ml<br>100 ml |
| 38 | 20.0095 | 10.0483 | 0.406 | 0 | 10.0222 | Methanol<br>Water | 720 ml<br>80 ml |
| 39 | 10.0139 | 5.0019 | 0.2019 | 0 | 5.0072 | Methanol<br>Water | 360 ml<br>40 ml |
| 40 | 10.0195 | 5.0092 | 0.2009 | 0 | 5.0098 | Methanol<br>Water | 360 ml<br>40 ml |

Dissolution Testing

Dissolution performance of a formulation in vivo is influenced by both the physicochemical properties of the substance and the prevailing physiological conditions in the gastrointestinal (GI) tract. Formulation composition generally influences in vitro drug dissolution and in vivo pharmacokinetics.

The Biopharmaceutical Classification System (BCS) classifies a drug product as rapidly dissolving when no less than 85% of the labeled amount of the drug substance dissolves in 30 minutes using the following:

USP Apparatus 1 (basket) at 100 rpm or USP Apparatus 2 (paddle) at 50 rpm.

Dissolution medium volume of 900 mL or less in each of the following:
0.1N HCl or simulated gastric fluid (SGF) USP without enzymes
A pH 4.5 buffer
A pH 6.8 buffer or simulated intestinal fluid (SIF) USP without enzymes In vitro dissolution testing is performed in order to arrive at desirable embodiments, including embodiments of immediate-release (IR) solid oral dosage forms for which bioequivalence may be assessed. Dissolution testing results are summarized in Table II. All testing is performed using USP Apparatus 2 (paddle) at 100 rpm in 900 mL dissolution medium ("media" in chart) volume, with a withdrawal sample of 10 mL, except that from minutes 60-70, testing is performed at 150 rpm. Formulation numbers ("Form'1 No.") in Table II are the same Formulation Numbers designated in Table I, except that the spray dried dispersion of Formulation No. 41 in Table II is a homogenous mixture of the spray dried dispersion of Formulation Nos. 37-40 from Table I. Dissolution testing is performed on spray dried dispersion formulations, with the exception of Formulation No. 42 in Table II, which is a gelatin capsule, the contents of which contain 200 mg API (metaxalone), in Formulation No. 41. While testing is performed in various discriminating conditions, it is noted that, because of the poor solubility of metaxalone, 0.5% SLS media is the official USP method, and for market release, dissolution is optimally at least 65 wt % at 60 minutes in such media.

TABLE II

| Form'l No. | Strength (mg) | Media | % Drug dissolved (wt %) Minutes | | | | | |
|---|---|---|---|---|---|---|---|---|
| | | | 10 | 20 | 30 | 45 | 60 | 70 |
| 9 | 400 | 0.1N HCl | 0 | 0 | 18 | 37 | 43 | 46 |
| 4 | 400 | 0.1N HCl | 28 | 49 | 63 | 71 | 75 | 77 |
| 5 | 400 | 0.1N HCl | 30 | 41 | 50 | 59 | 65 | 69 |
| 42 | 200 | 0.1N HCl | 30 | 46 | 60 | 70 | 78 | 87 |
| 14 | 400 | 0.1N HCl | 33 | 45 | 54 | 62 | 68 | 71 |
| 11 | 400 | 0.1N HCl | 39 | 50 | 57 | 64 | 68 | 72 |
| 12 | 400 | 0.1N HCl | 40 | 54 | 63 | 71 | 75 | 78 |
| 6 | 400 | 0.1N HCl | 44 | 62 | 73 | 83 | 88 | 91 |
| 35 | 400 | 0.1N HCl | 45 | 56 | 64 | 71 | 76 | 78 |
| 13 | 400 | 0.1N HCl | 45 | 60 | 68 | 75 | 79 | 81 |
| 20 | 560 | 0.1N HCl | 48 | 56 | 60 | 63 | 64 | 66 |
| 19 | 560 | 0.1N HCl | 49 | 56 | 60 | 62 | 64 | 64 |
| 33 | 400 | 0.1N HCl | 50 | 61 | 68 | 73 | 77 | 79 |
| 34 | 400 | 0.1N HCl | 51 | 66 | 75 | 83 | 87 | 90 |
| 18 | 560 | 0.1N HCl | 51 | 57 | 60 | 63 | 64 | 65 |
| 32 | 400 | 0.1N HCl | 57 | 72 | 79 | 85 | 89 | 90 |
| 30 | 200 | 0.1N HCl | 63 | 79 | 87 | 92 | 95 | NT |
| 31* 40 C./ 75% RH | 200 | 0.1N HCl | 66 | 84 | 90 | 93 | 94 | NT |
| 41 | 400 | 0.1N HCl | 69 | 80 | 85 | 89 | 90 | 91 |
| 29 | 200 | 0.1N HCl | 71 | 87 | 92 | 96 | 97 | NT |
| 42 | 200 | 0.1% SLS in pH 2.0 | 33 | 54 | 70 | 86 | 94 | 99 |
| 36 | 400 | 0.1% SLS in pH 2.0 | 36 | 77 | 85 | 92 | 96 | 98 |
| 26 | 800 | 0.1% SLS in pH 2.0 | 42 | 54 | 55 | 63 | 65 | 65 |
| 12 | 400 | 0.1% SLS in pH 2.0 | 46 | 65 | 73 | 83 | 88 | 91 |
| 5 | 400 | 0.1% SLS in pH 2.0 | 48 | 69 | 81 | 91 | 97 | CD |
| 21 | 400 | 0.1% SLS in pH 2.0 | 48 | 61 | 68 | 75 | 80 | 84 |
| 10 | 400 | 0.1% SLS in pH 2.0 | 52 | 64 | 72 | 78 | 83 | 85 |
| 19 | 560 | 0.1% SLS in pH 2.0 | 52 | 65 | 70 | 76 | 79 | 84 |
| 34 | 400 | 0.1% SLS in pH 2.0 | 54 | 72 | 83 | 93 | 98 | CD |
| 13 | 400 | 0.1% SLS in pH 2.0 | 56 | 74 | 85 | 92 | 96 | 98 |
| 20 | 560 | 0.1% SLS in pH 2.0 | 56 | NT | NT | NT | NT | NT |
| 19 | 560 | 0.1% SLS in pH 2.0 | 56 | 67 | 73 | NT | NT | NT |
| 27 | 800 | 0.1% SLS in pH 2.0 | 63 | 83 | 89 | 92 | CD | CD |
| 28 | 400 | 0.1% SLS in pH 2.0 | 65 | 83 | 90 | 95 | 98 | CD |
| 6 | 400 | 0.1% SLS in pH 2.0 | 71 | 88 | 96 | CD | CD | CD |
| 41 | 400 | 0.1% SLS in pH 2.0 | 73 | 86 | 92 | 96 | 97 | 98 |
| 26 | 800 | 0.5% SLS | 30 | 39 | 46 | 54 | 64 | 65 |
| 10 | 400 | 0.5% SLS | 46 | 68 | 82 | 94 | 99 | CD |
| 16 | 400 | 0.5% SLS | 46 | 65 | 78 | 90 | 95 | 99 |
| 36 | 800 | 0.5% SLS | 48 | 66 | 76 | 83 | 88 | 90 |
| 28 | 400 | 0.5% SLS | 51 | 69 | 77 | 85 | 90 | 93 |
| 7 | 400 | 0.5% SLS | 52 | 79 | 93 | CD | CD | CD |
| 16 | 400 | 0.5% SLS | 58 | 75 | 86 | 94 | 99 | CD |
| 24 | 800 | 0.5% SLS | 58 | 71 | 77 | 83 | 88 | 90 |
| 17 | 400 | 0.5% SLS | 59 | 81 | 93 | CD | CD | CD |
| 23 | 800 | 0.5% SLS | 60 | 75 | 83 | 89 | 93 | 95 |
| 25 | 800 | 0.5% SLS | 60 | 73 | 80 | 87 | 91 | 93 |
| 36 | 400 | 0.5% SLS | 61 | 79 | 88 | 94 | 97 | 98 |
| 22 | 800 | 0.5% SLS | 63 | 77 | 84 | 91 | 95 | 96 |
| 15 | 400 | 0.5% SLS | 70 | 92 | CD | CD | CD | CD |
| 27 | 800 | 0.5% SLS | 81 | 91 | 95 | 98 | CD | CD |
| 27 | 400 | 0.5% SLS | 82 | 93 | CD | CD | CD | CD |

TABLE II-continued

| Form'l No. | Strength (mg) | Media | % Drug dissolved (wt %) Minutes | | | | | |
|---|---|---|---|---|---|---|---|---|
| | | | 10 | 20 | 30 | 45 | 60 | 70 |
| 8 | 400 | FaSSGF | 0 | 0 | 30 | 38 | 43 | 46 |
| 2 | 400 | FaSSGF | 0 | 0 | 30 | 37 | 45 | 50 |
| 3 | 400 | FaSSGF | 0 | 37 | 47 | 56 | 63 | 68 |
| 21 | 400 | FaSSGF | 0 | 0 | 0 | 34 | 40 | 47 |
| 16 | 400 | FaSSGF | 0 | 9 | 32 | 42 | 50 | 53 |
| 1 | 400 | FaSSGF | 32 | 45 | 54 | 63 | 68 | 72 |
| 7 | 400 | FaSSGF | 37 | 51 | 61 | 71 | 79 | 84 |
| 5 | 400 | FaSSGF | 38 | 52 | 63 | 72 | 78 | 83 |
| 33 | 400 | FaSSGF | 39 | 53 | 60 | 66 | 69 | 72 |
| 15 | 400 | FaSSGF | 40 | 57 | 66 | 74 | 78 | 81 |
| 11 | 400 | FaSSGF | 41 | 52 | 59 | 66 | 71 | 75 |
| 12 | 400 | FaSSGF | 43 | 56 | 63 | 69 | 74 | 77 |
| 32 | 400 | FaSSGF | 43 | 59 | 70 | 78 | 83 | 86 |
| 19 | 560 | FaSSGF | 45 | 54 | 58 | 61 | 63 | 64 |
| 19 | 560 | FaSSGF | 46 | 54 | 58 | 61 | 63 | 64 |
| 35 | 400 | FaSSGF | 53 | 64 | 68 | 72 | 75 | 77 |
| 34 | 400 | FaSSGF | 57 | 72 | 81 | 87 | 91 | 94 |
| 29 | 200 | FaSSGF | 64 | 77 | 86 | 90 | 93 | NT |
| 31* 40 C./ 75% RH | 200 | FaSSGF | 69 | 84 | 89 | 93 | 96 | NT |
| 41 | 400 | FaSSGF | 69 | 79 | 84 | 87 | 90 | 92 |
| 30 | 200 | FaSSGF | 71 | 86 | 92 | 96 | 99 | NT |
| 25 | 800 | pH 2.0 | 0 | 18 | 27 | 39 | 48 | 50 |
| 25 | 800 | pH 6.8 | 45 | 58 | 63 | 65 | 67 | 70 |

NT = Not tested or data unavailable
CD = Complete dissolution
*For Form'l No. "31 40 C./75% RH", the samples were tested after Formulation No. 31 had been stored at 40° C./75% RH conditions for 6 weeks.

Analytical Characterization of Embodiment Formulation by XRPD Testing

FIG. 1 shows an XRPD diffractogram of Formulation No. 32.

Comparative In-Vitro Dissolution Testing

Comparative dissolution testing was performed (as described above) on the Reference Listed Drug (RLD), Skelaxin. Results are summarized in Table III.

TABLE III

| Skelaxin | | Time (min) % Dissolved (wt %) | | | | |
|---|---|---|---|---|---|---|
| Lot Number # 112687 | Media | 10 | 20 | 30 | 45 | 60 |
| Skelaxin Tablets*, 400 mg (Powdered tablets) | 0.1N HCl | 0 | 0 | 0 | 0 | 0 |
| | FaSSGF | 0 | 0 | 31 | 39 | 45 |

*The RLD tablets were crushed to produce a powder prior to dissolution testing for comparison with inventive SDD powder embodiments.

Figure 2:
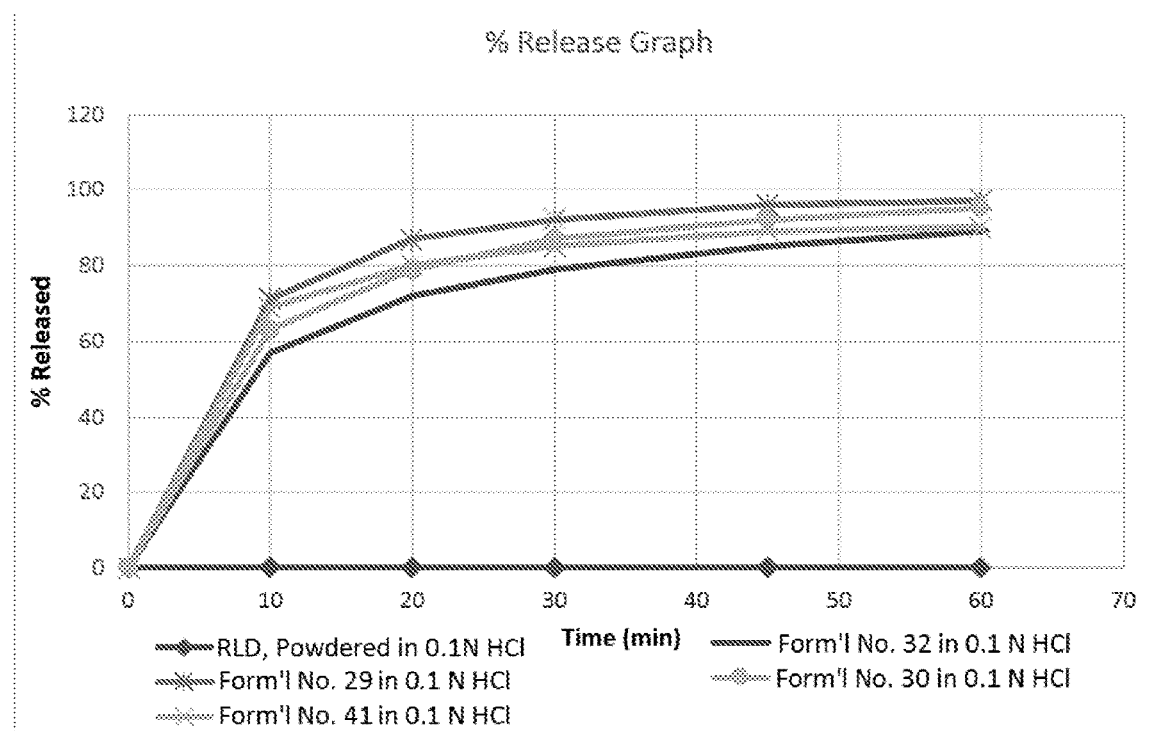
FIG. 2 is a chart comparing dissolution profiles in 0.1 N HCl media.

FIG. 2 is a chart comparing the dissolution profiles of powdered RLD from Table III and embodiments of inventive formulations in 0.1 N HCl media. As can clearly be seen, unlike inventive embodiments, even after being crushed, the RLD metaxalone tablets were practically insoluble.

Figure 3:
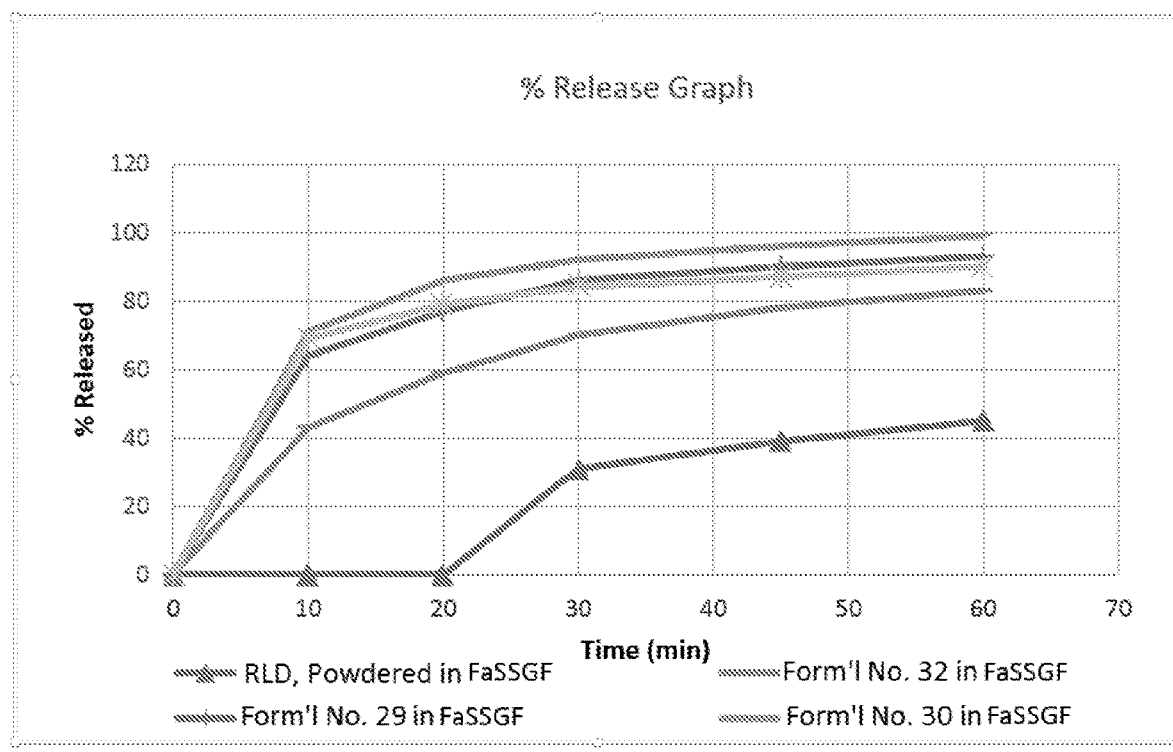
FIG. 3 is a chart comparing dissolution profiles in fasted simulated gastric fluid (FaSSGF).

FIG. 3 is a chart comparing the dissolution profiles of powdered RLD from Table III and embodiments of inventive formulations in fasted simulated gastric fluid (FaSSGF). As can clearly be seen, unlike inventive embodiments, even after being crushed, the RLD metaxalone tablets suffered from very poor solubility.

The in-vitro dissolution data indicate that the RLD is insoluble in 0.1 N HCl and poorly soluble in fasted simulated gastric fluid (FaSSGF). In contrast, inventive embodiment formulations, including Formulation Nos. 29, 30, 32, and 41 are soluble in both 0.1 N HCl and FaSSGF media, demonstrating that the inventive formulation embodiments have significantly improved solubility.

Solid-State Stability Testing

Figure 4C:
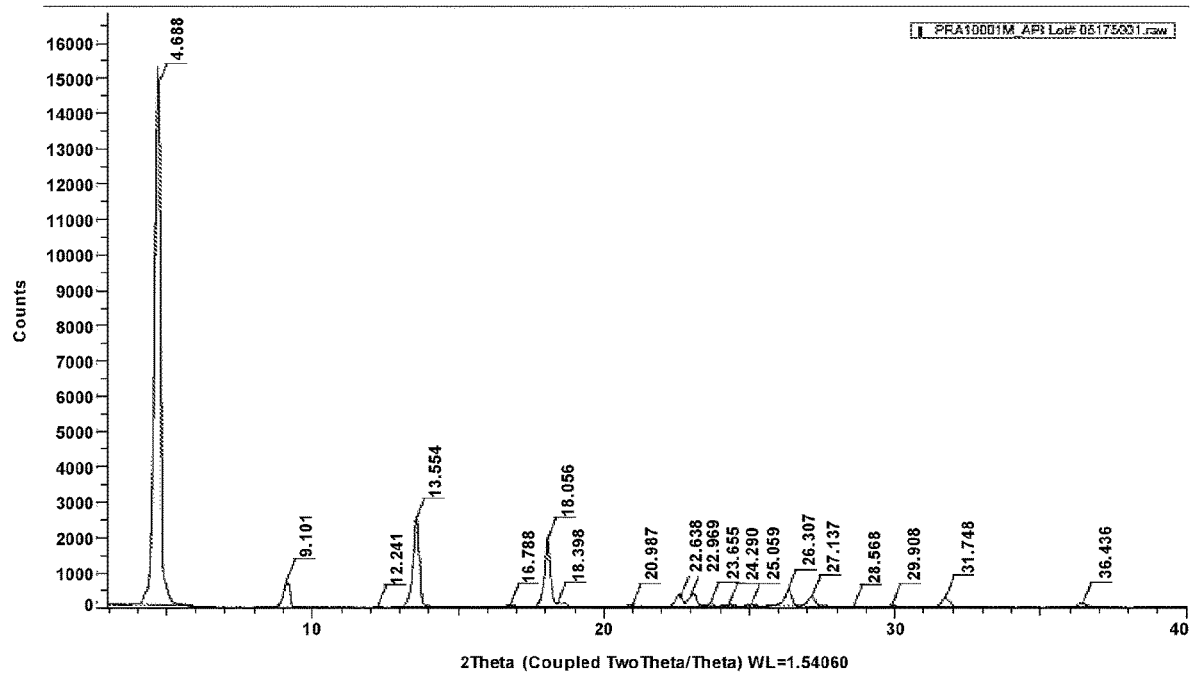
FIG. 4C is an XRPD diffractogram of metaxalone API powder.
Figure 4D:
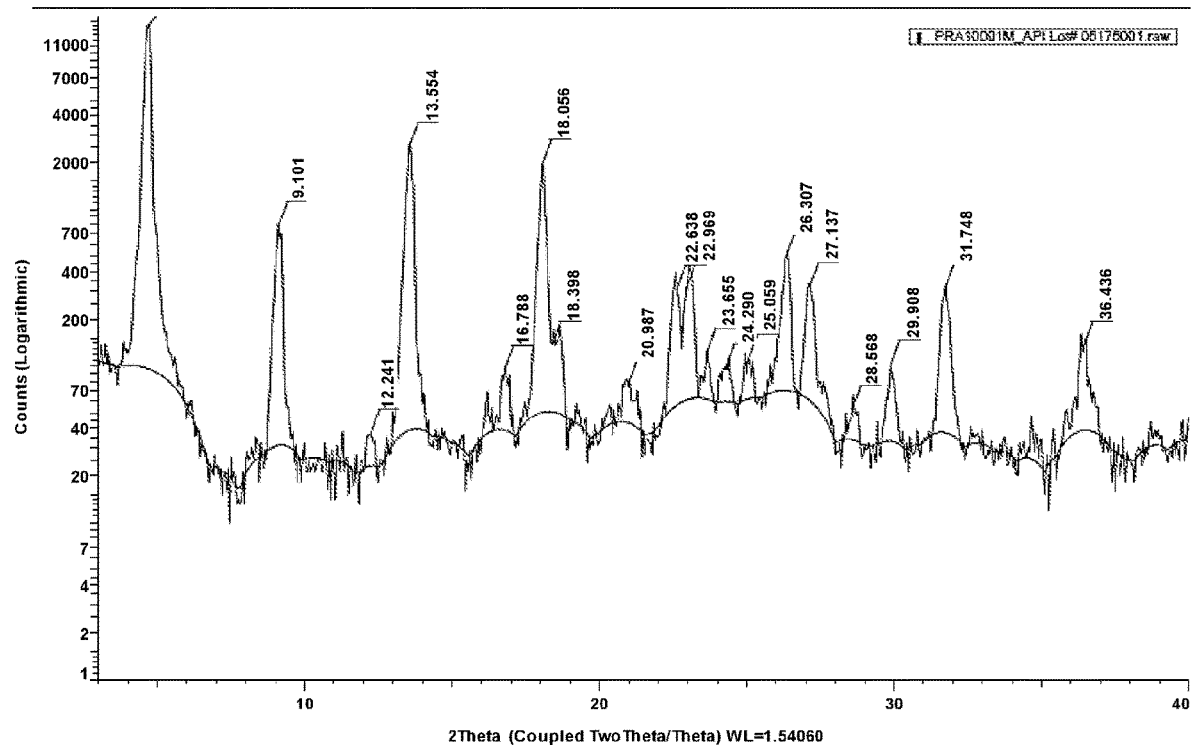
FIG. 4D is an enlarged portion of the XRPD diffractogram of FIG. 4B.

XRPD Studies. The solid-state stability of the Formulation No. 31 SDD powder was investigated at 40° C./75% RH conditions by X-Ray Powder Diffraction (XRPD) testing of samples stored at those conditions for 6 weeks. FIG. 4A is an XRPD diffractogram of Formulation No. 31 at t=0. FIG. 4B is an XRPD diffractogram of Formulation No. 31 at t=6 weeks after being stored at 40° C./75% RH. Some changes were observed in the XRPD pattern initially followed by minimal changes in subsequent time points. The initial changes in XRPD does not impact the dissolution of the SDD powder. On the other hand, FIG. 4C is an XRPD diffractogram of metaxalone API powder. A comparison of the inventive embodiment XRPD diffractograms with the API XRPD diffractogram shows the amorphous nature of inventive embodiments as compared to the API.

In-Vitro Dissolution Studies. The solid-state stability of the Formulation No. 31 SDD powder was investigated at 40° C./75% RH conditions by in-vitro dissolution testing of samples stored at those conditions for 6 weeks compared with initial data of representative batch. The dissolution profile did not show any change from T=0 to T=6 weeks.

Dosage Form Testing

G01 Capsules.

Capsule embodiments of the inventive formulations are prepared by filling gelatin capsule shells with the appropriate amount of SDD powder to achieve the desired dose. For the embodiments tested, gelatin shells are filled with a homogenous mixture of Formulation No. 29, and Formulation of No. 30. The capsule embodiments are herein designated as "G01 Capsules".

Figure 5A:
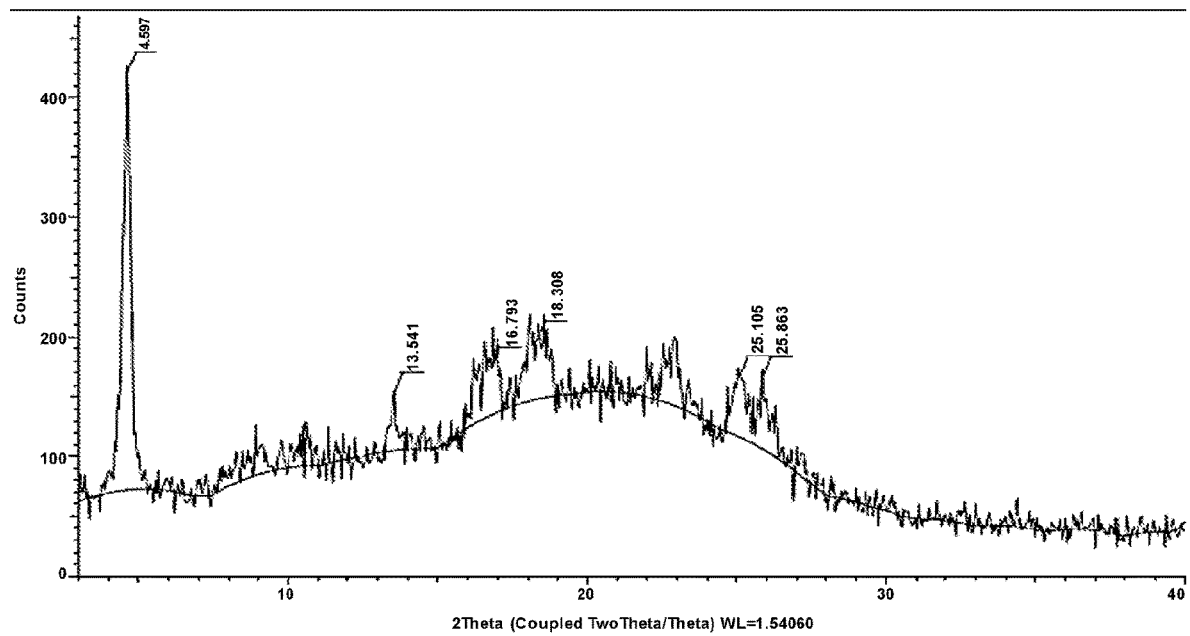
FIGS. 5A-C are XRPD diffractograms of a capsule embodiment at $T_0$ (FIG. 5A) and 3-months (FIG. 5B, 25° C./60% RH.
Figure 5B:
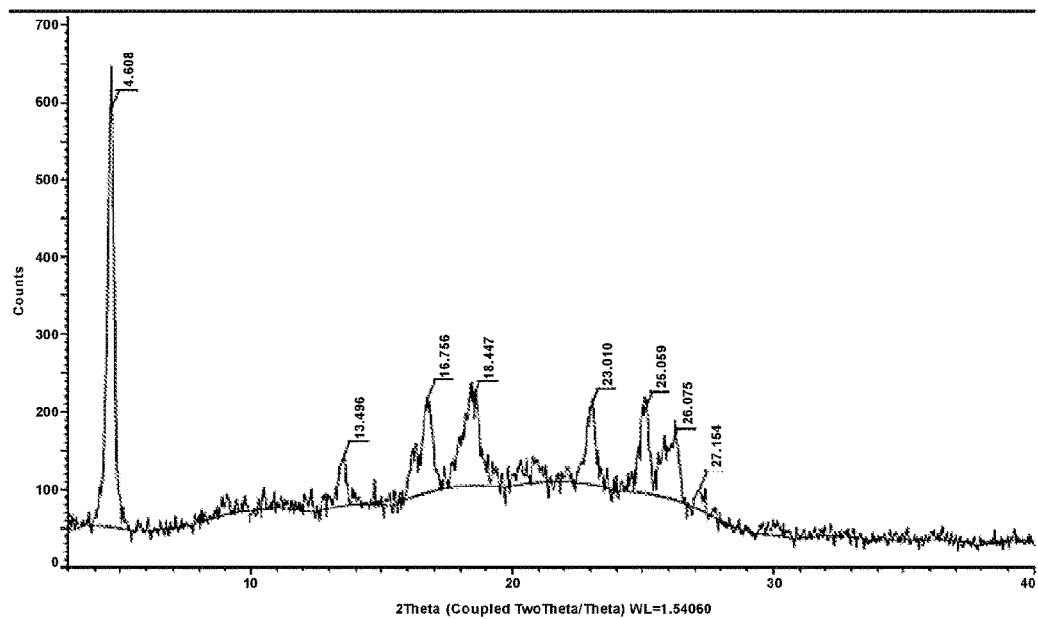
Figure 5C:
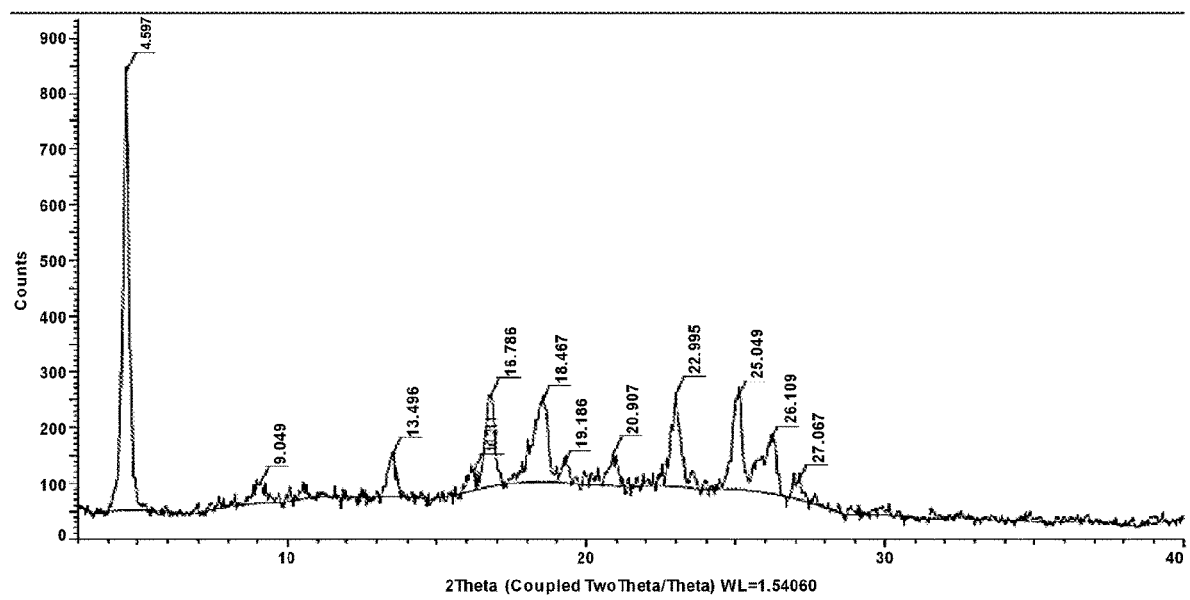

Solid-State Stability of SDD Powder in G01 Capsules by XRPD. The solid-state stability of the formulation in G01 Capsules (200 mg dose of metaxalone) was evaluated by XRPD testing of samples stored at 25° C./60% RH and 40° C./75% RH conditions for 3 months. FIGS. 5A-C are XRPD diffractograms of G01 Capsules at $T_0$ (5A) and 3-months (5B, 25° C./60% RH; 5C, 40° C./75% RH).

Solid-State Stability of SDD Powder in G01 Capsules—In-Vitro Dissolution. The solid-state stability of the formulation in G01 Capsules (200 mg dose) was evaluated by in-vitro dissolution testing of samples stored at 25° C./60% RH and 40° C./75% RH conditions for 3 months. The dissolution profiles at $T_0$ and 3-months are shown below in Table IV.

TABLE IV

| G01 Capsules | Media | Time (min) % Released (Wt %) | | | | |
|---|---|---|---|---|---|---|
| | | 10 | 20 | 30 | 45 | 60 |
| Initial | 0.1N HCl | 54 | 66 | 71 | 77 | 81 |
| 3 Months (25° C./60% RH) | 0.1N HCl | 48 | 66 | 76 | 89 | 95 |
| 3 Months (40° C./75% RH) | 0.1N HCl | 48 | 70 | 82 | 91 | 96 |

Both XRPD data and in-vitro dissolution data showed no significant changes, thus indicating the solid state stability of the inventive metaxalone SDD powder formulation in the G01 Capsules.

PRA Tablets.

200 mg pharmaceutical composition tablets are prepared. The tablets contain about 400 mg of Formulation No. 41 SDD powder (equivalent to 200 mg metaxalone API), about 50 mg crospovidone (disintegrant), about 55 mg croscarmellose (disintegrant), about 12 mg Aerosil 200 (lubricant/glidant), and about 12 mg magnesium stearate (lubricant/glidant). The tablet embodiment is herein designated as "PRA Tablet-200".

Dissolution testing (as described above) is performed on the PRA Tablet-200 tablets. Results are summarized in Table V-A. Using the same dissolution testing protocol as used for Table V-A, dissolution testing was also performed on RLD (Skelaxin) 400 mg tablets (where 400 mg RLD tablets are referred to herein, the 800 mg scored commercial tablets were cut in half, to provide a 400 mg tablet equivalent). Results are summarized in Table V-B.

TABLE V-A

| | Media | Time (min) % Released (wt %) | | | | |
|---|---|---|---|---|---|---|
| | | 10 | 20 | 30 | 45 | 60 |
| PRA Tablet-200 | 0.1N HCl | 55 | 71 | 80 | 87 | 91 |
| PRA Tablet-200 | FaSSGF | 58 | 77 | 86 | 94 | 99 |

TABLE V-B

| Skelaxin Tablets (RLD) Lot# 112687 | Media | Time (min) % Released (wt %) | | | | |
|---|---|---|---|---|---|---|
| | | 10 | 20 | 30 | 45 | 60 |
| Skelaxin Tablets, 400 mg | 0.1N HCl | 0 | 0 | 0 | 0 | 0 |
| Skelaxin Tablets, 400 mg | FaSSGF | 0 | 0 | 0 | 0 | 0 |

Figure 6:
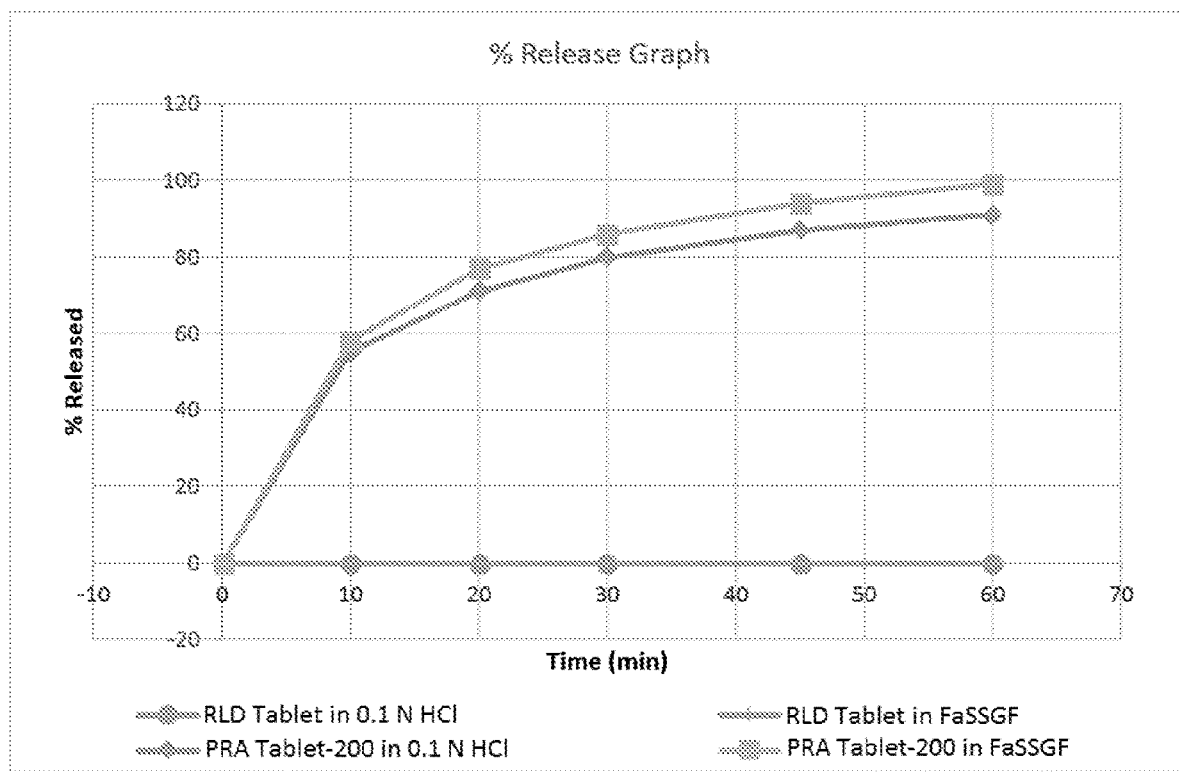
FIG. 6 is a chart comparing dissolution profiles of RLD (Skelaxin) tablets and tablets of an inventive embodiment in different media.

FIG. 6 is a chart comparing the dissolution profiles of 400 mg RLD tablets and PRA Tablet-200 from Tables V-A and V-B. As evident, unlike the inventive tablet embodiment that was tested, the RLD tablet showed no dissolution, even after 60 minutes.

The test data demonstrate that the biopharmaceutical properties of metaxalone are substantially improved via embodiments of the present invention, compared to the current reference product. In particular the dissolution data indicate that a more rapid rate of drug absorption and greater bioavailability occur in vivo. Another potential benefit of embodiments of the inventive formulation is that the food effect common with compounds of poor solubility and known to exist with the current marketed formulation may also be reduced.

Figure 7A:
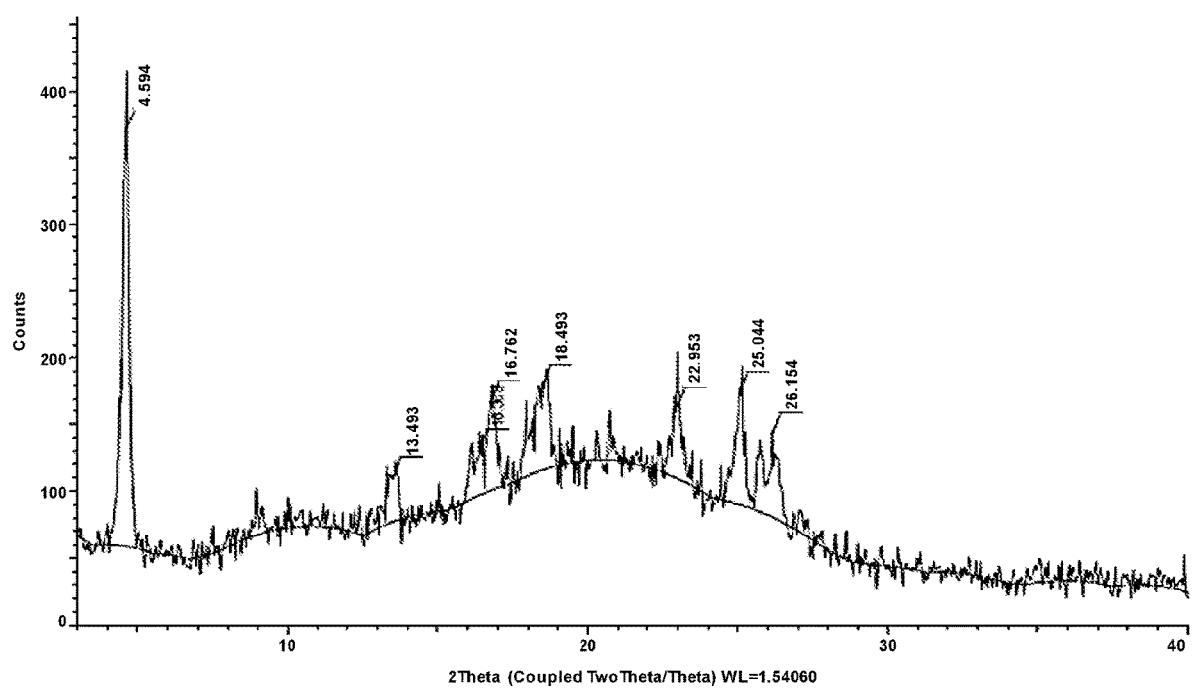
FIGS. 7A and 7B are XRPD diffractograms of an inventive tablet embodiment at $T_0$ (FIG. 7A) and 1 month 40° C./75% RH conditions (FIG. 7B).
Figure 7B:
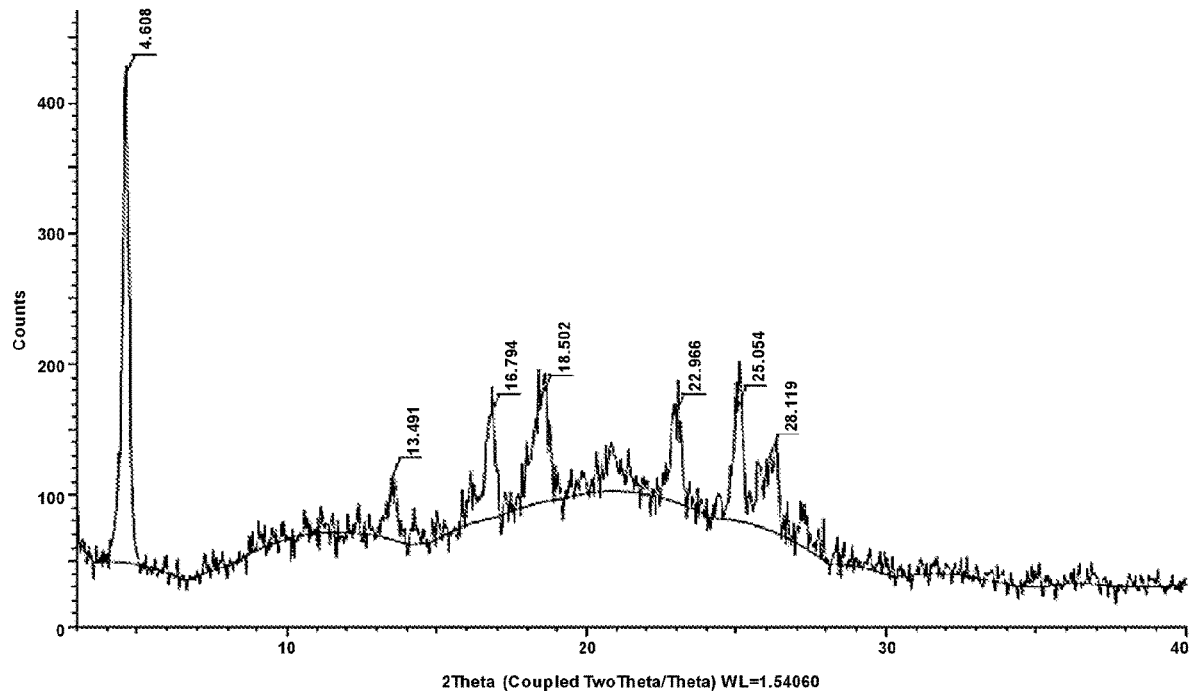

The solid-state stability of PRA Tablet-200 was evaluated by XRPD testing of samples at $T_0$ and stored at 40° C./75% RH conditions for 1 month. FIGS. 7A and 7B are XRPD diffractograms of PRA Tablet-200 at $T_0$ (FIG. 7A) and 1 month (FIG. 7B).

In-Vivo Bioequivalence/Relative Bioavailability Study

An in-vivo dog study is performed using 300 mg metaxalone. Specifically, the SDD of Formulation No. 31 was filled into gelatin capsules in an amount sufficient such that each capsule contained 300 mg metaxalone.

A pilot cross-over relative bioavailability study was conducted in 4 male beagle dogs given a single oral dose (300 mg of metaxalone, via gelatin capsules as described above) of the inventive embodiment (sprayed dried API from Formulation No. 31) and comparative equivalent of innovator product (Skelaxin tablet powder in a capsule, equivalent to 300 mg API). Blood samples were collected over a 24-hour period. Plasma concentrations of metaxalone were determined with a validated bioanalytical method. The limit of quantitation was 1 ng/mL (20 ng/mL for plasma retest) and all bioanalytical runs met standard acceptance criteria. Both dosage forms were administered as capsules. PK parameters, $C_{max}$, AUC, $t_{max}$ and $t_{1/2}$ (half life) were determined by standard non-compartmental methods. $C_{max}$ and AUC were considered the primary bioavailability PK parameters.

Figure 8:
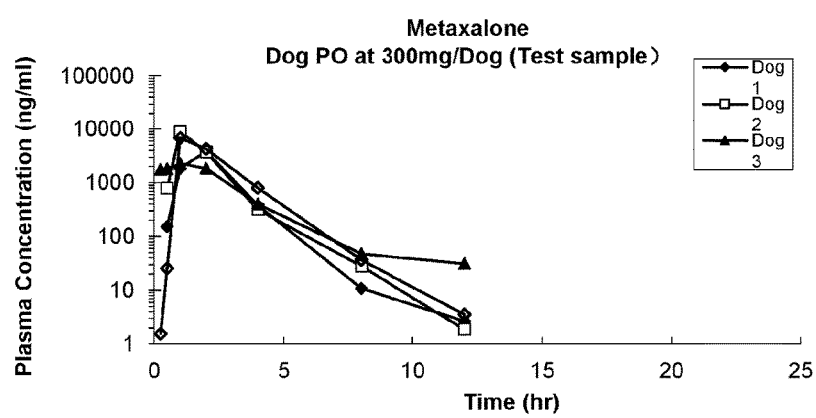
FIG. 8 is a chart showing individual animal plasma concentrations of metaxalone following a single 300 mg oral dose of an embodiment of the inventive formulation.
Figure 9:
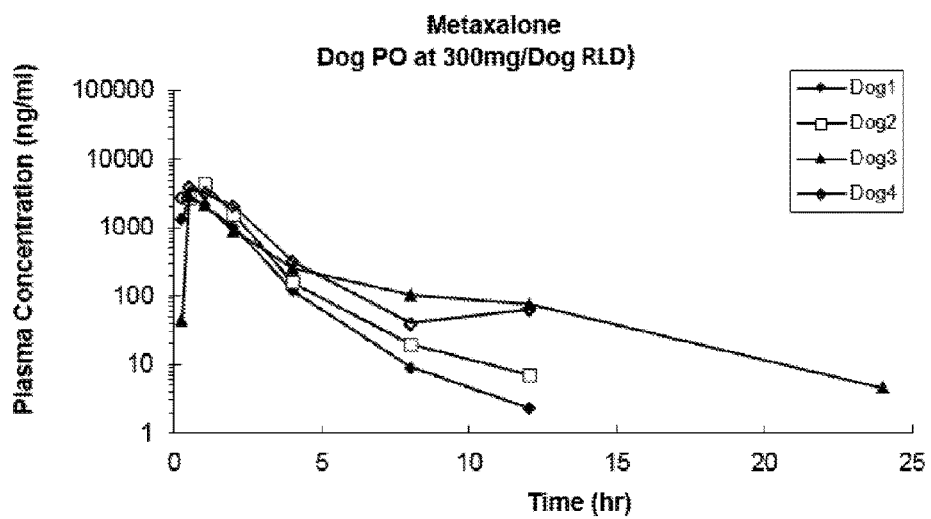
FIG. 9 is a chart showing individual animal plasma concentrations of metaxalone following a single 300 mg oral dose of the RLD (Skelaxin).

Measurable plasma concentrations of metaxalone appeared rapidly in the system following administration of both the test and reference dosage forms. The range in $t_{max}$ was 0.5-1 hour for the reference product and from 1-2 hours for the test formulation. In both cases plasma concentrations were observed generally for 12 hours post-dose. FIG. 8 is chart showing individual animal plasma concentrations of metaxalone following a single 300 mg oral dose of the inventive embodiment formulation. FIG. 9 is chart showing individual animal plasma concentrations of metaxalone following a single 300 mg oral dose (i.e., containing 300 mg API) of the RLD (Skelaxin) powder. Inspection of FIGS. 8 and 9 suggests that a somewhat more uniform individual subject concentration time course was observed with the inventive formulation embodiment. In addition, higher plasma levels were observed following administration of the inventive formulation embodiment.

Individual and mean dog PK parameters following an oral dose of 300 mg of either the inventive formulation embodiment or reference product (RLD powder) are presented in Table VI and Table VII, respectively. Maximum plasma concentrations of the test product were on average about 57% greater than the reference product and relative bioavailability was nearly 60% higher. The range in relative bioavailability was between 121 and 182%. Individual subject half-life tended to be slightly shorter following administration of the inventive formulation embodiment, which may be a subtle reflection of the increased rate of in vivo absorption exhibited by the inventive formulation embodiment, because no change in metabolism would be expected. In summary the pilot dog testing showed that the inventive formulation embodiment exhibited a faster rate and greater extent of absorption relative to the RLD product which was reflected in the comparative dissolution profile of the two products. This would suggest that the in vitro dissolution methodology can reflect in vivo performance of the two dosage forms.

TABLE VI

| Parameter | t½ (hr) | tmax (hr) | Cmax (ng/mL) | AUCInf (hr * ng/mL) | F (%) |
|---|---|---|---|---|---|
| | 1.12 | 2.00 | 3850 | 8419 | 175 |
| | 1.08 | 1.00 | 9080 | 13853 | 182 |
| | 2.17 | 1.00 | 2290 | 7175 | 121 |
| | 1.02 | 1.00 | 6800 | 14132 | 156 |

TABLE VI-continued

| Parameter | t½ (hr) | tmax (hr) | Cmax (ng/mL) | AUCInf (hr * ng/mL) | F (%) |
|---|---|---|---|---|---|
| N | 4 | 4 | 4 | 4 | 4 |
| Mean | 1.35 | 1.25 | 5505 | 10895 | 159 |
| SD | 0.55 | 0.50 | 3029 | 3615 | 28 |
| CV(%) | 40.8 | 40.0 | 55.0 | 33.2 | 17.4 |

TABLE VII

| Parameter | t½ (hr) | tmax (hr) | Cmax (ng/mL) | AUCInf (hr*ng/mL) |
|---|---|---|---|---|
| | 1.42 | 0.50 | 2740 | 4898 |
| | 1.79 | 1.00 | 4440 | 7671 |
| | 3.37 | 0.50 | 2900 | 5888 |
| | 1.77 | 0.50 | 3920 | 9051 |
| N | 4 | 4 | 4 | 4 |
| Mean | 2.09 | 0.625 | 3500 | 6877 |
| SD | 0.87 | 0.250 | 816 | 1848 |
| CV (%) | 41.9 | 40.0 | 23.3 | 26.9 |

Human Bioequivalence Study

In order to compare human exposure to an embodiment of the inventive formulation against the innovator reference product (Skelaxin Tablets), a standard two way-two period cross-over bioequivalence study in 8 healthy subjects was performed. Subjects received a 400 mg dose of an embodiment of the inventive formulation as a capsule (G01 Capsule). The reference product was given as a split tablet (i.e., one half of an 800 mg tablet), which represented the same 400 mg dose administered using the inventive embodiment. Blood samples for the determination of plasma concentrations of metaxalone were collected over a 24 hour period and there was a 6-day washout period between the two treatment phases. A validated LC-MS/MS bioanalytical method with a limit of quantitation of ~2 ng/mL was used. All bioanalytical runs meet standard acceptance criteria. Subjects were fasted overnight for at least 10 hours prior to drug administration and all subjects completed the study.

Figure 10:
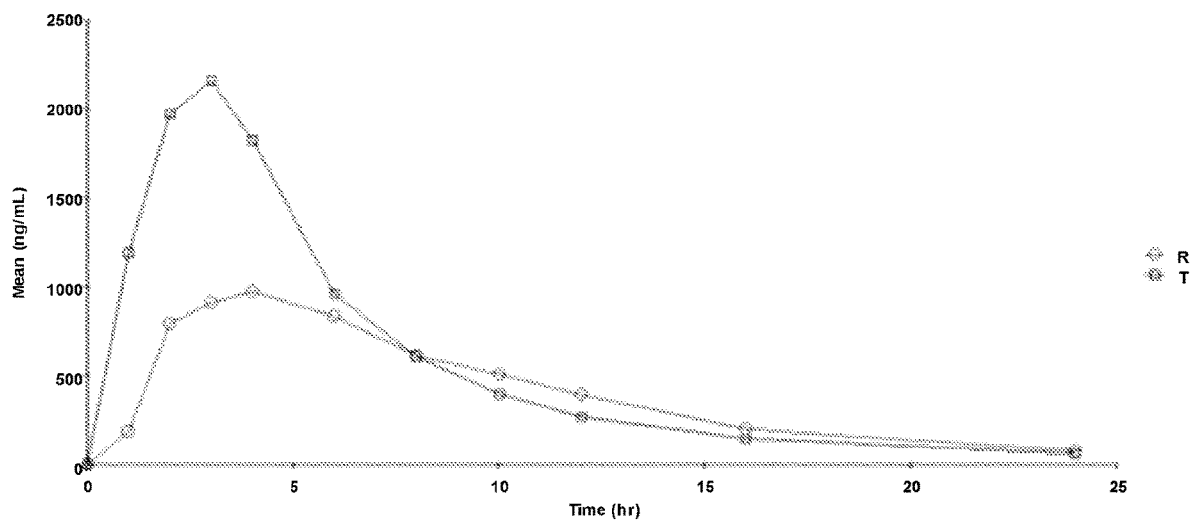
FIG. 10 is a graph showing mean plasma concentrations of metaxalone (ng/mL) following oral administration of 400 mg of an embodiment of the inventive formulation (squares) or reference RLD (Skelaxin) dosage form (circles).

Measurable plasma concentrations of metaxalone were seen in all subjects 1 hour post dose and also 24 hours post dose (with a single exception). All pre-dose plasma concentrations were below the limit of quantitation, indicating that the washout period was of sufficient duration. Maximum plasma concentrations of metaxalone were systematically greater in subjects given the embodiment of the inventive formulation and its occurrence tended to be faster as well (see FIG. 10, which is a graph showing mean plasma concentrations of metaxalone (ng/mL) following oral administration of 400 mg of an embodiment of the inventive formulation (squares) or reference RLD dosage form (circles)). The mean metaxalone pharmacokinetic parameters following oral administration of the reference and inventive embodiment products are presented in Table VIII and Table IX, respectively.

TABLE VIII

Descriptive PK Statistics of the Reference Product (RLD)
Following Oral Administration of 400 mg of Metaxalone

| Pharmacokinetic Parameter | N | Arithmetic Mean ± Standard Deviation | Coefficient of Variation | Median | Minimum | Maximum |
|---|---|---|---|---|---|---|
| $C_{max}$ (ng/mL) | 8 | 1161.1403 ± 654.8582 | 56.3979 | 1082.7825 | 414.2660 | 2128.3290 |
| $AUC_{0-t}$ (ng · hr/mL) | 8 | 9983.3808 ± 6372.3583 | 63.8297 | 8279.0363 | 3159.0350 | 18685.4280 |
| $AUC_{0-\infty}$ (ng · hr/mL) | 8 | 10625.7240 ± 6892.7816 | 64.8688 | 8634.1428 | 3351.7647 | 20880.2292 |
| $t_{max}$ (hr) | 8 | 3.6250 ± 1.6850 | 46.4833 | 3.5000 | 2.0000 | 6.0000 |
| $K_{el}$ (1/hr) | 8 | 0.1467 ± 0.0375 | 25.5319 | 0.1371 | 0.1002 | 0.2166 |

TABLE VIII-continued

Descriptive PK Statistics of the Reference Product (RLD)
Following Oral Administration of 400 mg of Metaxalone

| Pharmacokinetic Parameter | N | Arithmetic Mean ± Standard Deviation | Coefficient of Variation | Median | Minimum | Maximum |
|---|---|---|---|---|---|---|
| $t_{1/2}$(hr) | 8 | 4.9775 ± 1.1605 | 23.3147 | 5.0550 | 3.2000 | 6.9200 |
| $AUC\_{\%Extrap\_obs}$ | 8 | 5.8525 ± 2.8828 | 49.2583 | 6.3450 | 1.1800 | 10.5100 |

TABLE IX

Descriptive PK Statistics of Inventive Embodiment Formulation
Following Oral Administration of 400 mg of Metaxalone

| Pharmacokinetic Parameter | N | Arithmetic Mean ± Standard Deviation | Coefficient of Variation | Median | Minimum | Maximum |
|---|---|---|---|---|---|---|
| $C_{max}$ (ng/mL) | 8 | 2439.3090 ± 1510.2235 | 61.9119 | 1818.4270 | 1416.7350 | 5887.6630 |
| $AUC_{0-t}$ (ng · hr/mL) | 8 | 13926.0826 ± 9249.5243 | 66.4187 | 11176.3350 | 5285.1780 | 32233.3310 |
| $AUC_{0-\infty}$ (ng · hr/mL) | 8 | 18502.1194 ± 13825.8073 | 74.7255 | 16019.8545 | 5518.6717 | 43902.6108 |
| $t_{max}$ (hr) | 8 | 2.2500 ± 0.8864 | 39.3958 | 2.5000 | 1.0000 | 3.0000 |
| $K_{el}$ (1/hr) | 8 | 0.1718 ± 0.1226 | 71.3546 | 0.1460 | 0.0046 | 0.4187 |
| $t_{1/2}$(hr) | 8 | 22.6713 ± 51.8987 | 228.9186 | 4.7600 | 1.6600 | 151.0500 |
| $AUC\_{\%Extrap\_obs}$ | 8 | 11.5763 ± 27.1126 | 234.2086 | 2.3650 | 0.3100 | 78.5900 |

The bioequivalence statistical analysis is shown in Table X.

TABLE X

Bioequivalence Statistical Analysis (Anti-log Scale)

| Pharmacokinetic Parameter | Least Square Mean Test Product (T) | Reference Product (R) | ISCV (%) | T/R Ratio (%) | Power (%) | 90% Confidence Interval |
|---|---|---|---|---|---|---|
| $C_{max}$ (ng/mL) | 2159.65 | 994.6659 | 20.81 | 217.11 | 49.97 | 177.74 TO 265.21 |
| $AUC_{0-t}$ (ng · hr/mL) | 11578.44 | 8097.414 | 13.07 | 143.00 | 84.94 | 126.02 TO 162.27 |
| $AUC_{0-\infty}$ (ng · hr/mL) | 14289.78 | 8604.151 | 47.48 | 166.09 | 16.58 | 107.18 TO 257.38 |

The rate and extent of in vivo absorption was greater following oral administration of the inventive capsule. The bioequivalence analysis demonstrated that Cmax and AUC were 2-fold and 66% greater than the reference tablet, respectively. In addition a smaller $t_{max}$ was observed with the test product which is also indicative of a faster rate of drug absorption and in vivo dissolution. The median half-lives were similar which suggested that in vivo clearance and volume of distribution were consistent in this study. (Median comparisons were used because one outlier half-life of 151 hours was reported in 1 subject given the test product.) The results of the pilot bioequivalence study clearly demonstrate that the inventive embodiment exhibited both a greater rate and extent of absorption when compared to Skelaxin tablets.

The formulation development program and in vitro dissolution testing data from various bio-relevant media described supra were found to be qualitatively predictive of improved bioavailability outcome in an animal model. The proof of concept relative bioavailability studies demonstrated the same result not only in animal model but also in humans. Taken together the in vitro dissolution, pre-clinical dog model and proof of concept study in healthy human subjects establish advantageous properties of embodiments of the invention, including significantly improved biopharmaceutical properties, including those relative to dissolution and bioavailability.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), "contain" (and any form contain, such as "contains" and "containing"), and any other grammatical variant thereof, are open-ended linking verbs. As a result, a method or article that "comprises", "has", "includes" or "contains" one or more steps or elements possesses those one or more steps or elements, but is not limited to possessing only those one or more steps or elements. Likewise, a step of a method or an element of an article that "comprises", "has", "includes" or "contains" one or more features possesses those one or more features, but is not limited to possessing only those one or more features.

As used herein, the terms "comprising," "has," "including," "containing," and other grammatical variants thereof encompass the terms "consisting of" and "consisting essentially of."

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed compositions or methods.

All publications cited in this specification are herein incorporated by reference as if each individual publication were specifically and individually indicated to be incorporated by reference herein as though fully set forth.

Subject matter incorporated by reference is not considered to be an alternative to any claim limitations, unless otherwise explicitly indicated.

Where one or more ranges are referred to throughout this specification, each range is intended to be a shorthand format for presenting information, where the range is understood to encompass each discrete point within the range as if the same were fully set forth herein.

While several aspects and embodiments of the present invention have been described and depicted herein, alternative aspects and embodiments may be affected by those skilled in the art to accomplish the same objectives. Accordingly, this disclosure and the appended claims are intended to cover all such further and alternative aspects and embodiments as fall within the true spirit and scope of the invention.

The invention claimed is:

1. A pharmaceutical composition comprising:
   40 to 60 wt % metaxalone or a pharmaceutically acceptable salt thereof;
   0.2 to 5 wt % sodium lauryl sulfate;
   15 to 35 wt % hydroxypropyl methylcellulose (HPMC); and
   15 to 35 wt % copolymer of vinylpyrrolidone and vinyl acetate.

2. The pharmaceutical composition according to claim 1, for oral administration as a solid dosage form.

3. The pharmaceutical composition according to claim 2, in the form of a tablet or capsule.

4. The pharmaceutical composition according to claim 3, in the form of a tablet.

5. The pharmaceutical composition according to claim 1, wherein the copolymer of vinylpyrrolidone and vinyl acetate is a copolymer of formula (I):

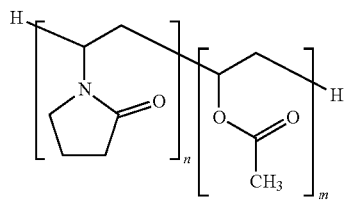

(I)

wherein 0.8 m≤n≤1.6 m.

6. The pharmaceutical composition according to claim 1, comprising:
   45 to 55 wt % metaxalone or pharmaceutically acceptable salt thereof;
   0.5 to 2 wt % sodium lauryl sulfate;
   20 to 30 wt % HPMC; and
   20 to 30 wt % copolymer of vinylpyrrolidone and vinyl acetate.

7. The pharmaceutical composition according to claim 6, comprising:
   48 to 52 wt % metaxalone or pharmaceutically acceptable salt thereof;
   0.8 to 1.2 wt % sodium lauryl sulfate;
   23 to 27 wt % HPMC; and
   23 to 27 wt % copolymer of vinylpyrrolidone and vinyl acetate.

8. The pharmaceutical composition according to claim 1, comprising 200 mg metaxalone or a pharmaceutically acceptable salt thereof.

9. The pharmaceutical composition according to claim 1, comprising 400 mg metaxalone or a pharmaceutically acceptable salt thereof.

10. The pharmaceutical composition according to claim 1, comprising 800 mg metaxalone or a pharmaceutically acceptable salt thereof.

11. The pharmaceutical composition according to claim 1, additionally comprising one or more further agents.

12. The pharmaceutical composition according to claim 11, wherein the one or more further agents comprise at least one member that is a disintegrant, diluent, glidant, lubricant, acidulant, stabilizer, suspending agent, filler, binder, plasticizer, release aid, or other pharmaceutically acceptable carrier, excipient, or adjuvant.

13. The pharmaceutical composition according to claim 1, wherein said composition is in the form of a spray-dried amorphous dispersion.

14. The pharmaceutical composition according to claim 1, said composition having improved solubility, bioavailability, $C_{max}$ and/or $t_{max}$ as compared to metaxalone pharmaceutical compositions that are not formulated with the sodium lauryl sulfate, hydroxypropyl methylcellulose (HPMC), and copolymer of vinylpyrrolidone and vinyl acetate.

15. A method of treating musculoskeletal pain or a musculoskeletal condition comprising the step of administering to a patient in need thereof a pharmaceutical composition according to claim 1.

* * * * *